United States Patent [19]
Tearney et al.

[11] Patent Number: 6,134,003
[45] Date of Patent: Oct. 17, 2000

[54] METHOD AND APPARATUS FOR PERFORMING OPTICAL MEASUREMENTS USING A FIBER OPTIC IMAGING GUIDEWIRE, CATHETER OR ENDOSCOPE

[75] Inventors: Guillermo Tearney, Cambridge; Stephen A. Boppart; Brett E. Bouma, both of Boston; Mark Brezinski, Malden; Eric A. Swanson, Acton; James G. Fujimoto, Cambridge, all of Mass.

[73] Assignee: Massachusetts Institute of Technology, Cambridge, Mass.

[21] Appl. No.: 08/607,787

[22] Filed: Feb. 27, 1996

Related U.S. Application Data

[63] Continuation-in-part of application No. 08/492,738, Jun. 21, 1995, and a continuation-in-part of application No. 08/577,366, Dec. 12, 1995, and a continuation-in-part of application No. 08/252,940, Jun. 2, 1994, which is a continuation of application No. 08/033,194, Mar. 16, 1993, Pat. No. 5,459,570, which is a continuation of application No. 07/692,877, Apr. 29, 1991, abandoned.

[51] Int. Cl.[7] ............................................. G01B 9/02
[52] U.S. Cl. .......................... 356/345; 356/349; 356/351
[58] Field of Search ................................ 356/345, 349, 356/351

[56] References Cited

U.S. PATENT DOCUMENTS

| | | |
|---|---|---|
| 4,171,159 | 10/1979 | White . |
| 4,420,260 | 12/1983 | Martinelli . |
| 4,545,390 | 10/1985 | Leary . |
| 4,554,929 | 11/1985 | Samson et al. . |
| 4,596,466 | 6/1986 | Ulrich . |
| 4,612,938 | 9/1986 | Dietrich et al. . |
| 4,619,274 | 10/1986 | Morrison . |
| 4,648,892 | 3/1987 | Kittrell et al. . |
| 4,652,129 | 3/1987 | Martinelli . |
| 4,669,465 | 6/1987 | Moore et al. . |

(List continued on next page.)

FOREIGN PATENT DOCUMENTS

| | | |
|---|---|---|
| 3627420 A1 | 2/1987 | Germany . |
| 60-235005 | 11/1985 | Japan . |
| 04135552 | 5/1992 | Japan . |
| 2 191 855A | 12/1987 | United Kingdom . |
| 953/3970 | 12/1995 | WIPO . |

OTHER PUBLICATIONS

Park et al., "High Resolution Optical Ranging System", *Applied Optics*, vol. 20, No. 14, pp. 2389–2394 (Jul. 15, 1981).

(List continued on next page.)

*Primary Examiner*—Robert H. Kim

[57] ABSTRACT

An imaging system for performing optical coherence tomography includes an optical radiation source; a reference optical reflector; a first optical path leading to the reference optical reflector; and a second optical path coupled to an endoscopic unit. The endoscopic unit preferably includes an elongated housing defining a bore; a rotatable single mode optical fiber having a proximal end and a distal end positioned within and extending the length of the bore of the elongated housing; and an optical system coupled to the distal end of the rotatable single mode optical fiber, positioned to transmit the optical radiation from the single mode optical fiber to the structure and to transmit reflected optical radiation from the structure to the single mode optical fiber. The system further includes a beam divider dividing the optical radiation from the optical radiation source along the first optical path to the reflector and along the second optical path; and a detector positioned to receive reflected optical radiation from the reflector transmitted along the first optical path and reflected optical radiation transmitted from the structure along the second optical path. The detector generates a signal in response to the reflected optical radiation from the reference reflector and the reflected optical radiation from the structure, and a processor generating a image of the structure in response to the signal from the detector. The system provides both rotational and longitudinal scanning of an image.

16 Claims, 18 Drawing Sheets

U.S. PATENT DOCUMENTS

| | | |
|---|---|---|
| 4,669,467 | 6/1987 | Willett et al. . |
| 4,718,417 | 1/1988 | Kittrell et al. . |
| 4,721,117 | 1/1988 | Mar et al. . |
| 4,748,986 | 6/1988 | Morrison et al. . |
| 4,796,994 | 1/1989 | Bager . |
| 4,819,632 | 4/1989 | Davies . |
| 4,844,062 | 7/1989 | Wells . |
| 4,873,989 | 10/1989 | Einzig . |
| 4,899,733 | 2/1990 | DeCastro et al. . |
| 4,900,314 | 2/1990 | Quackenbush . |
| 4,913,142 | 4/1990 | Kittrell et al. .............................. 606/7 |
| 4,928,005 | 5/1990 | Lefèet al. . |
| 4,958,930 | 9/1990 | Robertson, Jr. . |
| 4,969,736 | 11/1990 | Slotwinski . |
| 5,005,584 | 4/1991 | Little . |
| 5,053,033 | 10/1991 | Clarke . |
| 5,094,534 | 3/1992 | Cole et al. . |
| 5,104,392 | 4/1992 | Kittrell et al. . |
| 5,106,387 | 4/1992 | Kittrell et al. . |
| 5,110,211 | 5/1992 | Niki et al. . |
| 5,114,403 | 5/1992 | Clarke et al. . |
| 5,133,598 | 7/1992 | Badeau . |
| 5,157,457 | 10/1992 | Taylor . |
| 5,196,004 | 3/1993 | Sinofsky . |
| 5,197,470 | 3/1993 | Helfer et al. . |
| 5,201,317 | 4/1993 | Kanazawa et al. . |
| 5,202,745 | 4/1993 | Sorin et al. . |
| 5,217,456 | 6/1993 | Narciso, Jr. .............................. 606/15 |
| 5,268,738 | 12/1993 | Baney et al. . |
| 5,268,741 | 12/1993 | Chou et al. . |
| 5,291,267 | 3/1994 | Sorin et al. . |
| 5,305,759 | 4/1994 | Kaneko et al. .......................... 128/665 |
| 5,321,501 | 6/1994 | Swanson et al. . |
| 5,325,177 | 6/1994 | Peterson .................................. 356/357 |
| 5,365,335 | 11/1994 | Sorin . |
| 5,383,467 | 1/1995 | Auer et al. . |
| 5,390,023 | 2/1995 | Biegen .................................... 356/359 |
| 5,439,000 | 8/1995 | Gunderson et al. . |
| 5,459,570 | 10/1995 | Swanson et al. . |
| 5,589,938 | 12/1996 | Deck ....................................... 356/359 |

OTHER PUBLICATIONS

Clivaz et al., "High–resolution reflectometry in biological tissues", *Optics Letters*, vol. 17, No. 1, pp. 4–6 (Jan., 1992).

Takada et al., "Phase–noise and shot–noise limited operations of low coherence optical time domain reflectometry", *Appl. Phys. Lett.*, vol. 59, No. 20, pp. 2483–2485 (Nov., 1991).

Fercher et al., "Eye–length measurement by interferometry with partially coherent light", *Optics Letters*, vol. 13, No. 3 pp. 186–188 (Mar., 1988).

Beaud et al., "Optical Reflectometry with Micrometer Resolution for the Investigation of Integrated Optical Devices", *Journal of Quantum Electronics*, vol. 25, No. 4, pp. 755–759 (Apr., 1989).

Hitzenberger, "Optical Measurement of the Axial Eye Length by Laser Doppler Interferometry", *Investigative Ophthalmology & Visual Science*, vol. 32, No. 3, pp. 616–624 (Mar., 1991).

Youngquist et al., "Optical coherence–domain reflectometry: a new optical evaluation technique", *Optics Letters*, vol. 12, No. 3, pp. 158–160 (Mar., 1987).

Takada et al., "New measurement system for fault location in optical waveguide devices based on an interferometric technique", *Applied Optics*, vol. 26, No. 9, pp. 1603–1605 (May, 1987).

Danielson et al., "Guided–wave reflectometry with micrometer resolution", *Applied Optics*, vol. 26, No. 14, pp. 2836–2842 (Jul., 1987).

Gilgen et al., "Submillimeter Optical Reflectometry", *Journal of Lightwave Technology*, vol. 7, No. 8, pp. 1225–1233 (Aug., 1989).

Tateda et al., "Water Penetration Sensing Using Wavelength Tunable OTDR*", *IEEE Photonics Technology Letters*, vol. 3, No. 1, pp. 1–3 (Jan., 1991).

Kobayashi et al., "Polarization–Independent Interferometric Optical–Time–Domain Reflectometer", *Journal of Lightwave Technology*, vol. 9, No. 5, pp. 623–628 (May, 1991).

Kobayashi et al., "Optical Fiber Component Characterization by High–Intensity and High–Spatial–Resolution Interferometric Optical–Time–Domain Reflectometer,", *IEEE Photonics Technology Letters*, vol. 3, No. 6, pp. 564–566 (Jun., 1991).

Takada et al., "Rayleigh backscattering measurement of single–mode fibers by low coherence optical time–domain reflectometer with 14 $\mu$m spatial resolution", *Appl. Phys. Lett.*, vol. 59, No. 2, pp. 143–145 (Jul., 1991).

Takada et al., "Resolution Control of Low–Coherence Optical Time–Domain Reflectometer Between 14 and 290 ∞m", *IEEE Photonics Technology Letters*, vol. 3, No. 7, pp. 676–678 (Jul., 1991).

Huang et al., "Micron–Resolution Ranging of Cornea Anterior Chamber by Optical Reflectometry", *Lasers in Surgery and Medicine*, vol. 11, pp. 419–425 (1991).

Sorin et al., "Simultaneous Thickness and Group Index Measurement Using Optical Low–Coherence Reflectometry", *IEEE Photonics Technology Letters*, vol. 4, No. 1, pp. 105–107 (Jan., 1992).

Swanson et al., "High–speed optical coherence domain reflectometry", *Optics Letters*, vol. 17, No. 2, pp. 151–153 (Jan., 1992).

Hitzenberger et al., "Measurement of Corneal Thickness by Laser Doppler Interferometry", *Investigative Ophthalmology & Visual Science*, vol. 33, No. 1, pp. 98–103 (Jan., 1992).

Huang et al., "Optical Coherence Tomography", *Science*, vol. 254, pp. 1178–1181 (Nov., 1991).

Potkin et al., "Coronary artery imaging with intravascular high–frequency ultrasound", *Circulation*, vol. 81, No. 5, pp. 1575–1585 (May, 1990).

Brezinski et al., "Optical coherence tomography for optical biopsy properties and demonstration of vascular pathology", *Circulation* vol. 93, No. 6 (Mar., 1996).

Tearney et al., "Optical biopsy in human tissue using optical coherence tomography and microscopy", *CLEO* (Conference on Lasers and Electro–Optics), (May, 1995).

Chornenky, "Low–Coherence Interferometry in Coronary Arteries", *Coronary Artery Diseases*, vol. 6, No. 5, pp. 377–380 (May, 1995).

Swanson et al., "Optical Coherence Tomography: Principles, Instrumentation, and Biological Applications", *Biomedical Optical Instrumentation and Laser–Assisted Biotechnology*, (Nov., 1995), Ercie, Italy.

Izatt et al., "Optical Coherence Microscopy in Scattering Media", *Optics Letters*, vol. 19, No. 8 pp. 590–592 (Apr., 1994).

Yadlowsky et al., "Multiple Scattering in Optical Coherence Microscopy", *Applied Optics*, vol. 34, No. 25, pp. 5699–5707 (Sep., 1995).

Chinn et al., "Blindness Limitations in Optical Coherence Domain Reflectometry", *Electronics Letters*, vol. 29, No. 23 pp. 2025–2027 (Nov., 1993).

Bouma et al., "High–Resolution Optical Coherence Tomographic Imaging using a Mode–Locked Ti:A1O$_3$ Laser Source", *Optics Letters*, vol. 20, No. 13, pp. 1486–1488 (Jul., 1995).

Morioka et al., "Near Penalty–Free<4 ps Supercontinuum WDM Pulse Generation for Tbit/s TDM–WDM Networks", *Proc. Optical Fiber Comm.*, Paper PD21-1 (1995).

DeSouza et al., "Spectrally Sliced WDM using a Single Femtosecond Source", *Proc. Optical Fiber Comm.*, Paper PD16-1, (1995).

Hee et al, "Polarization Sensitive Low Coherence Reflectometer for Birefringence Characterization and Ranging", *Journal of Optical Society of America B*, vol. 9, No. 6, pp. 903–908 (Jun., 1992).

Izat, et al., "Micrometer–Scale Resolution Imaging of the Anterior Eye in Vivo with Optical Coherence Tomography", *Archives of Ophthalmology*, vol. 112, pp. 1584–1589 (Dec., 1994).

Hee et al., "Quantitative Assessment of Macular Edema with Optical Coherence Tomography", *Archives of Ophthalmology*, vol. 113, pp. 1019–1029, (Aug., 1995).

Puliafito et al., "Imaging of Macular Diseases with Optical Coherence Tomography", *Ophthalmology*, vol. 102, No. 2, pp. 217–229 (Feb., 1995).

Clivaz et al., "1.5$\mu$ Resolution Optical Low Coherence Reflectometry in Biological Tissues", *SPIE Proc.*, vol. 2083, No. 19, pp. 1–9 (1994).

Schmitt et al. "Measurement of optical properties of biological tissues by low–coherence reflectometry", *Applied Optics*, vol. 32, No. 30, pp. 6032–6042 (Oct., 1993).

Schmitt et al., "Optical –coherence tomography of a dense tissue: statistics of attenuation and backscattering", *Phys. Med. Biol.*, vol. 39, pp. 1705–1720 (1994).

Tearney et al., "Optical Coherence Tomography in multiply scattering tissues", *SPIE*, vol. 2389, pp. 29–34 (Proceedings of Optical Tomography, Photon Migration, and Spectroscopy of Tissue and Model Media: Theory, Human Studies, and Instrumentation), (Feb., 1995).

Sergeev et al., "High–spatial–resolution optical–coherence tomography of human skin and mucous membranes", Conference on Lasers and Electro–Optics, (May, 1995).

Yock et al., "Intravascular Ultrasound Guidance for Catheter–Based Coronary Interventions,"*JACC*, vol. 17, No. 6, pp. 39B–45B (May, 1991).

Fujimoto et al. "Optical biopsy and imaging using optical coherence tomography", *Nature Medicine*, vol. 1, No. 9, pp. 970–972 (Sep., 1995).

Brezinski et al., "Imaging of Coronary Artery Microstructure (In vitro) With Optical Coherence Tomography", *The American Journal of Cardiology*, Vo. 77 (2 pages) (Jan., 1996).

Gelikonov, V.M., "Coherent optical tomography of microscopic inhomogeneities in biological tissues", No. 2 *American Institute of Physics*, pp. 158–162 (Jan. 25, 1995).

Sergeev, A., et als., "In Vivo Optical Coherence Tomography of Human Skin Microstructure", presented at BIOS Europe, Sep. 1994, Proc. SPIE, v. 2328, pp. 144–153.-

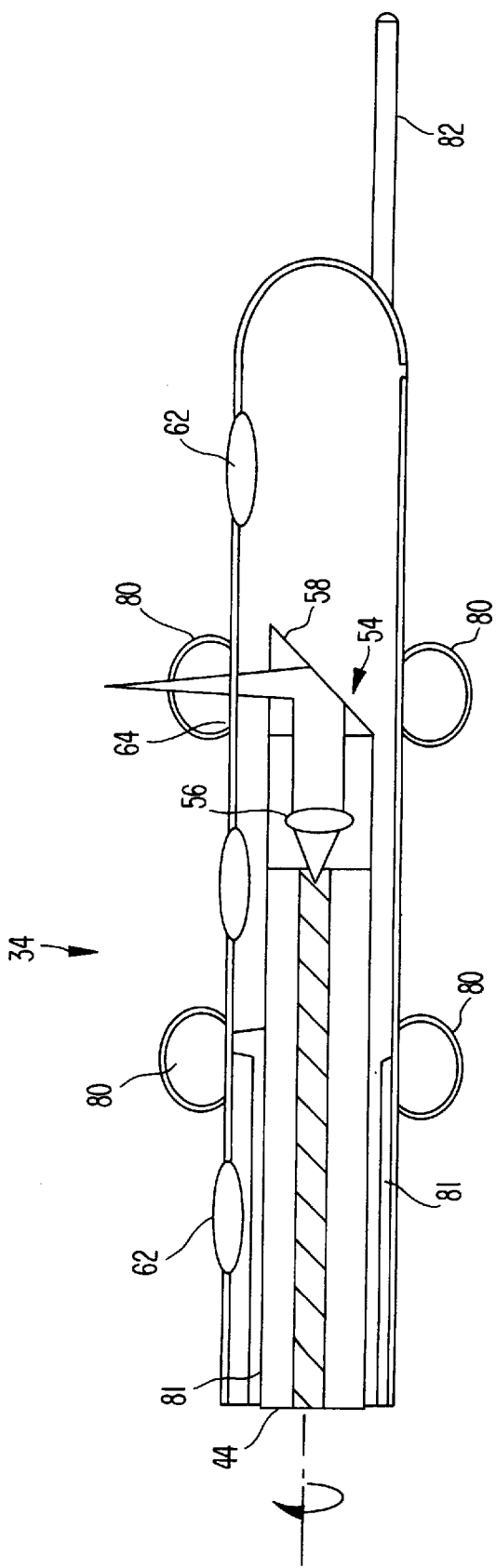
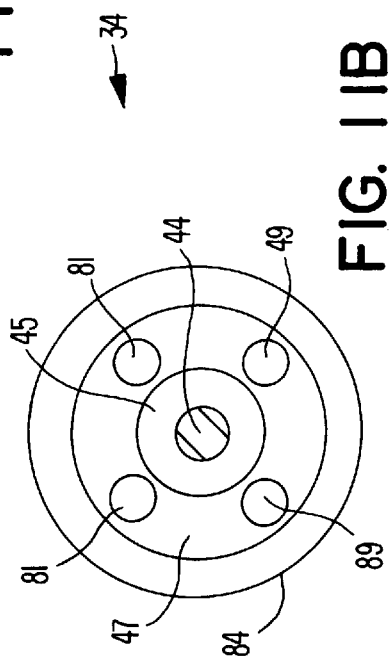
FIG. 11A
FIG. 11B

METHOD AND APPARATUS FOR PERFORMING OPTICAL MEASUREMENTS USING A FIBER OPTIC IMAGING GUIDEWIRE, CATHETER OR ENDOSCOPE

CROSS-REFERENCE TO A RELATED APPLICATION

This application is a continuation in part of U.S. Ser. No. 08/492,738, filed on Jun. 21, 1995, pending; and is a continuation in part of Ser. No. 08/577,366, filed on Dec. 12, 1995, pending; and is a continuation in part of U.S. Ser. No. 08/252,940, filed on Jun. 2, 1994, pending, which is a continuation in part of Ser. No. 08/033,194, filed on Mar. 16, 1993, now U.S. Pat. No. 5,459,570, which is a continuation of Ser. No. 07/692,877, filed on Apr. 29, 1991, now abandoned, the contents of which are all incorporated herein by reference.

STATEMENT REGARDING FEDERALLY SPONSORED RESEARCH

This invention was made with government support under Contract Numbers NIH-5-R01-GM35459-09 and NIH-9-R01-EY11289-10 awarded by the National Institute of Health, and Contract Number N00014-94-1-0717 awarded by the Department of the Navy. The U.S. government has certain rights in the invention

FIELD OF INVENTION

This invention relates to the field of optical imaging and more specifically to the field of medical imaging with interferometric detection.

BACKGROUND OF THE INVENTION

Over the past decade there have been tremendous advances in biomedical imaging technology. For example, magnetic resonance imaging, X-ray computed tomography, ultrasound, and confocal microscopy are all in widespread research and clinical use, and have resulted in fundamental and dramatic improvements in health care. However, there are many situations where existing biomedical diagnostics are not adequate. This is particularly true where high resolution (~1 μm) imaging is required. Resolution at this level often requires biopsy and histopathologic examination. While such examinations are among the most powerful medical diagnostic techniques, they are invasive and can be time consuming and costly. Furthermore, in many situations conventional excisional biopsy is not possible. Coronary artery disease, a leading cause of morbidity and mortality, is one important example of a disease where conventional diagnostic excisional biopsy can not be performed. There are many other examples where biopsy can not be performed or conventional imaging techniques lack the sensitivity and resolution for definitive diagnosis.

Moreover, for medical procedures such as balloon angioplasty, conventional techniques have not been able to provide high resolution imaging of the artery while a balloon is being inflated. Many other interventional procedures would greatly benefit from high resolution, in-vivo visualization technology. This technology would be useful for performing preoperative and post-operative diagnostics, to alert medical personnel to problems, or to avoid problems encountered during medical procedures.

The present invention seeks to overcome the problems associated with such conventional imaging techniques.

SUMMARY OF THE INVENTION

It is an object of this invention to provide an endoscopic imaging system that provides high resolution images and is useful during a medical procedure to enable medical personnel to view a procedure or actively help control the procedural process while it is occurring. In one embodiment the optical imaging system comprises an endoscopic unit and an interferometer for performing multi-dimensional scanning of a structure by utilizing an optical coherence tomography (OCT) technique. In one embodiment, the present invention uses OCT to perform high resolution imaging of structures. OCT measures the optical properties of a structure interferometrically using a short coherence length or frequency tunable light source.

In one embodiment the system includes an interferometer which includes a broadband optical radiation source; an optical radiation detector; a reference optical reflector; a first optical path leading to the reference optical reflector; and a second optical path including an endoscopic unit. The endoscopic unit, in one embodiment, includes an elongated housing defining a bore, within which is positioned a rotatable single mode optical fiber extending the length of the bore of the elongated housing. In an alternative embodiment, the endoscopic unit of the present invention includes a fixed fiber and rotatable optical beam directing elements at the distal end of the endoscopic unit. An optical beam directing system is coupled to the distal end of the rotatable single mode optical fiber and is positioned to transmit the optical radiation from the single mode optical fiber to the structure and to transmit reflected optical radiation from the structure to the single mode optical fiber. The optical beam directing system of the endoscopic unit typically includes a lens and a beam director located at the distal end of the single mode optical fiber and positioned to direct light from the single mode optical fiber to the structure. The beam director may include a prism, a lens or a mirror and may be driven from a motor external to the endoscope via a mechanical linkage, or may be driven from a micromotor.

The endoscopic unit also includes a transparent window typically formed at the distal end of the housing or around the circumference of the distal end thereof to permit the transmission of optical radiation to and from the structure. Additionally, an irrigation port may be formed in the housing for delivering fluid to the structure in question. The endoscopic unit can further include one or more inflatable balloons for performing procedures such as balloon angioplasty, for maintaining the opening in a vessel.

The interferometer of the system further includes a beam divider which divides the optical radiation from the optical radiation source along the first optical path to the reflector and along the second optical path to the structure being viewed. The optical radiation detector is positioned to receive reflected optical radiation from the reflector and reflected optical radiation from the structure and to generate a signal in response to the reflected optical radiation. A processor utilizes the signals from the detector to generate an image of the structure being viewed.

In one embodiment the reference optical reflector is typically coupled to a movable actuator to provide periodic movement to the reference mirror. In another embodiment the movable reference mirror is replaced with a static reference mirror and the broadband optical source replaced with a narrow bandwidth frequency tunable source, such as a semiconductor laser with tunable external gratings, a tunable solid state laser, or a dye laser. With such a source, optical radiation reflected from the structure being observed will arrive at the detector after the radiation reflected from the reference mirror is received at the detector. If the source is frequency modulated this delay will result in a beat frequency that is dependent on the difference between the distance from the detector to the reflection site within the structure, and the distance from the detector to the reference reflector. In still other embodiments of the present invention, the detector forming part of the imaging system includes a polarization diversity receiver, or alternatively a polarization analyzer. In still another embodiment the source consists of a broad band optical source, an interferometric detector using an optical spectrum analyzer wherein the Fourier transform of the spectrum is used to derive the reflectance profile of the sample.

It should be noted, that as used herein, the term endoscopic, applies to medical as well as non-medical imaging. One example of non-medical imaging in which the present invention may be used is as a replacement for a borescope to detect faults in cavities and bores in various industrial applications. For purposes of discussion only, the description to follow describes the present invention in terms of medical imaging, but the it is not the intent to limit the applications so described herein. Furthermore although the term endoscope is used, this invention directly relates to guidewires, catheters, and imaging with probes placed through trocars.

BRIEF DESCRIPTION OF DRAWINGS

FIG. 11A depicts an alternate embodiment of the endoscopic unit of the present invention which includes inflatable balloons.

FIG. 11B depicts the embodiment of FIG. 11A in cross-section.

DETAILED DESCRIPTION OF THE INVENTION

Figure 1:
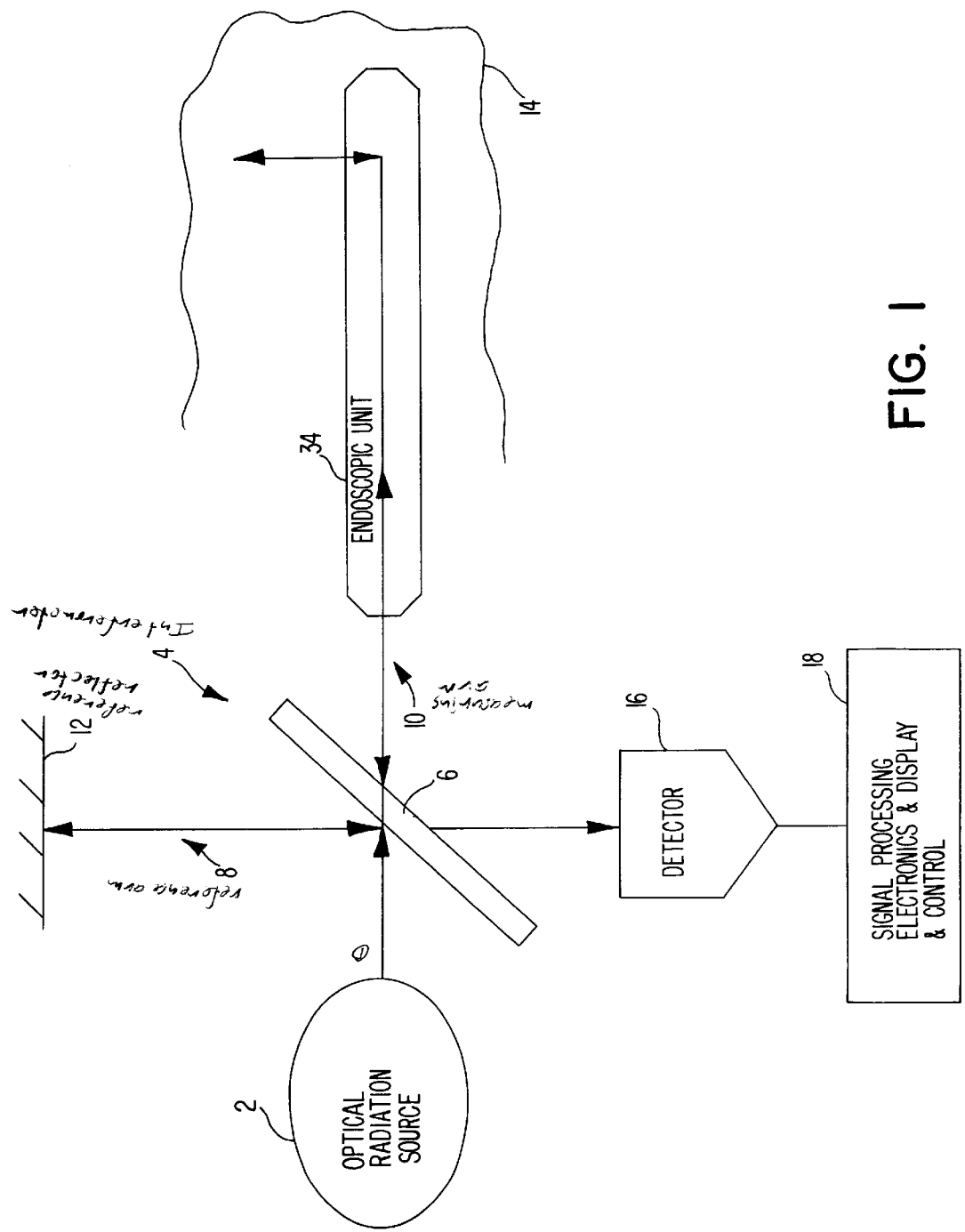
FIG. 1 is a block diagram of an embodiment of the imaging system of the present invention.

The imaging system of the present invention is broken down into a several major subsystems as shown in FIG. 1. In general, the imaging system includes an optical radiation source 2, an interferometer 4, a detector 16, and an endoscopic unit 34. The interferometer 4 may be of any of the types known to one skilled in the art. For the purposes of discussion only, the embodiment will be discussed in terms of a Michelson interferometer. However, other embodiments using the other types of interferometers are contemplated. The interferometer 4 of this embodiment includes a beam divider 6 which divides the optical radiation along a first optical path defining a reference arm 8 and a second optical path defining a measuring arm 10. The optical path defining a reference arm 8 includes a reference reflector 12. The optical path defining the measuring arm 10 includes the endoscopic unit 34.

In general, the interferometer 4 operates by transmitting radiation from the optical radiation source 2 to the beam divider 6 where it is divided and transmitted along the optical paths defining the reference arm 8 and the measuring arm 10. Light reflected from the beam divider 6 travels along the reference arm 8 and is reflected back by the reference reflector 12. Light transmitted through the beam divider 6 along the measuring arm 10 travels through the endoscopic unit 34 and illuminates a structure 14 under observation. Light reflected by the structure 14 travels back through the endoscopic unit 34 along the measuring arm 10 to the beam divider 6. The radiation reflected from the reference reflector 12 and the radiation reflected from the structure 14, are then recombined by the beam divider 6 and transmitted to the detector 16. The resulting combined radiation generates an interference pattern at the detector 16 which typically generates electrical signals representative of the combined radiation and transmits these signals to signal processing and control electronics and display unit 18 where an image of the structure is obtained and analyzed.

By changing the length of the reference arm 8, longitudinal scanning is accomplished. Longitudinal scanning provides a way of changing the location at which interference in the optical radiation being reflected from the structure 14 back through the endoscopic unit 34 is detected. If the optical radiation is emitted off axis to the longitudinal axis of the endoscopic unit 34, such scanning provides a means of viewing different tissue depths. In one embodiment, the length of the reference arm 8 is changed by moving the reference reflector 12.

By rotating the optical radiation beam emitted from the endoscopic unit 34, rotational scanning may be accomplished. In rotational scanning, a circumferential path whose radius is centered at the longitudinal axis of the endoscopic unit 34 is viewed.

Optical Sources

Considering each component in more detail, the optical source 2 has characteristics such as wavelength, power, coherence length, and autocorrelation function which are important factors in system performance. In some applications, near infrared sources (1.0–2.0 um) tend to penetrate deeper into many biological media than visible wavelengths and are therefore preferable. The optical radiation source 2 can include in various embodiments: semiconductor sources (light emitting diodes (LED), edge emitting diodes (ELED), superluminscent diodes (SLD), mode-lock lasers (e.g. $TiAl_2O_3$, $Cr:Mg_2SiO_4$, $CrLiSrAlF_6$), rare earth doped fibers (REDF) (Yb, Nd, Er, Pr, Tm), and super-continuum or Raman sources. For REDF in order to obtain a good coherence length and autocorrelation function, it may be necessary to insert short period Bragg gratings or long period Bragg gratings into the fiber or use filters external to the fiber to shape the Amplified Spontaneous Emission spectrum (ASE). LED and ELED devices are very-low cost broad bandwidth devices having coherence lengths less than 10 $\mu$m. Their main limitation is that typically they have very low power (<100 $\mu$W) when coupled into a single spatial mode. SLDs typically have a short coherence length of about ~10 $\mu$m, and power of about ~2 $\mu$W. Actively and passively mode-locked lasers offer very high power (>100 mW) and short coherence length (<5 $\mu$m). Additionally, source powers in excess of 100 mW and coherence lengths under 10 $\mu$m can be used. Spectrally shaped REDF, particularly cladding pumped fibers offer good performance in many applications.

Interferometers

Figure 2B:
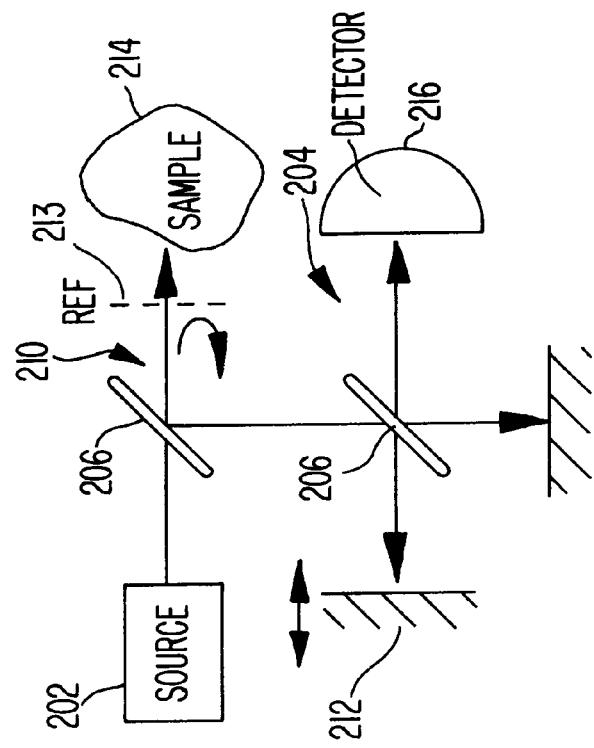
FIG. 2A and 2B depict interferometers used in the imaging system of FIG. 1
Figure 2A:
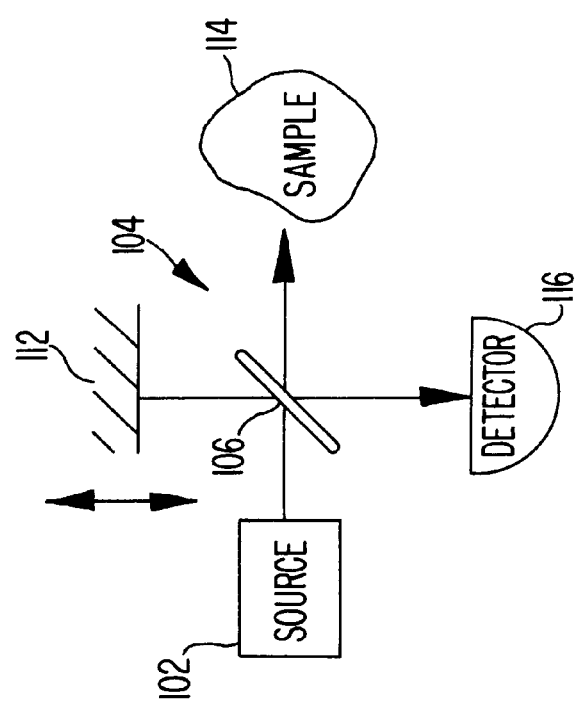

Referring to FIGS. 2A and 2B, there are several varieties of interferometers that may be used in the system of the present invention. Although bulk optical and free space implementations are shown in these figures, there exist equivalent embodiments employing optical fibers. One embodiment employs a simple Michelson Interferometer 104, as shown in FIG. 2A. In another embodiment, as shown in FIG. 2B, the interferometer 204 includes a sample reference reflector 206 in the measuring arm 210. The use of this reference reflector 206 in the measuring arm 210 allows for long displacements between beamsplitter 211 and sample 14.

Although faster scanning helps eliminate motion induced artifacts, in most living biological tissues there is a limit to how fast scanning can be accomplished due to the finite signal power that can safely be delivered to the specimen or practical considerations in mechanical scanning systems. Signal processing techniques can help eliminate any residual motion induced artifacts as is described later. As shown in the interferometer 204 of FIG. 2B, by placing a sample reference reflector 206 near or on the structure, a differential measurement between the sample reference reflector and structure is possible. This measurement is less sensitive to any path length variations along the measurement arm 210. In fact the distance to the structure 14 can be made very large. In order to maintain sensitivity, the sample reference reflector 206 must reflect enough radiation to maintain shot-noise-limited operation. The sample reference reflector 206 can be located at the distal end of the endoscopic unit 34 to help overcome potential artifacts caused by the delivery optics.

Figure 3:
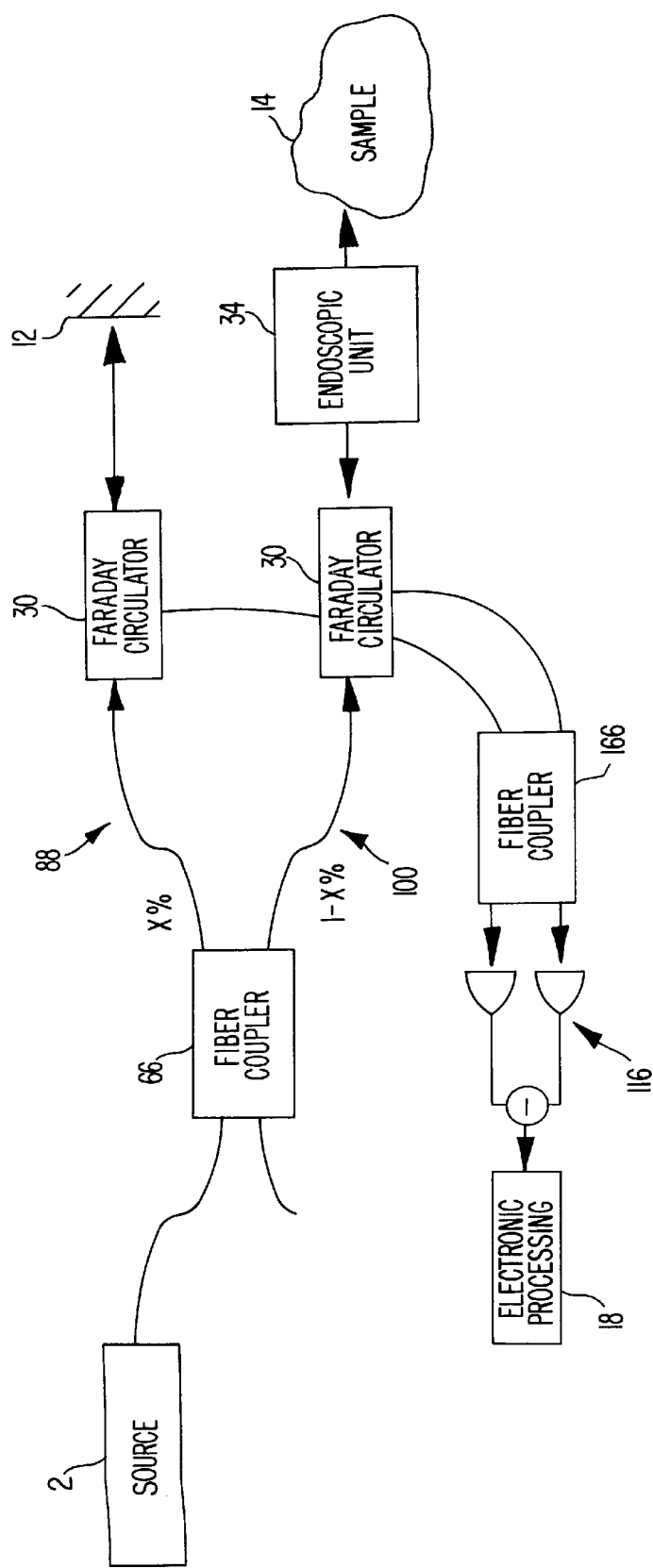
FIG. 3 shows the imaging system of FIG. 1 employing fiber optics, Faraday circulators and a balanced receiver.

In the interferometers 104 and 204 described in FIG. 2A and 2B, at least 3 dB of signal power from the structure under observation is lost as radiation is directed back toward the optical source 2. An additional 3 dB of power is directed toward the reference mirror 12 where it is often attenuated, and therefore wasted. Referring to FIG. 3, another embodiment of the imaging system of the present invention is shown which employs Faraday circulators 30 to overcome this limitation. A polarization insensitive Faraday circulator is a three port device with the property of separating incoming and outgoing light. The Faraday circulators 30, rather than directing radiation reflected along the reference arm 88 and measuring arm 100 to the optical coupler 66, direct the reflected radiation to a fiberoptic coupler 166 associated with the detector, which in this embodiment includes a balanced receiver 116. For an ideal lossless circulator 3 dB more signal power is delivered to the balanced receiver 116, as compared to the case where the detector receives the reflected radiation from the optical coupler 66. In addition the coupler 66 need not divide the radiation equally (50/50). In a preferred embodiment only a small percentage of the signal power is delivered to the reference arm 88, with the remainder being sent to the measuring arm 100. The amount of energy sent to the reference arm 8 is determined by the minimum power required to obtain shot-noise-limited detection. The output of the fiber coupler is sent to a dual balanced receiver to make maximum use of the received reference and sample signal power and so as to cancel excess intensity noise and ASE×ASE noise in the receiver.

Longitudinal Scanning Mechanisms

Figure 4:
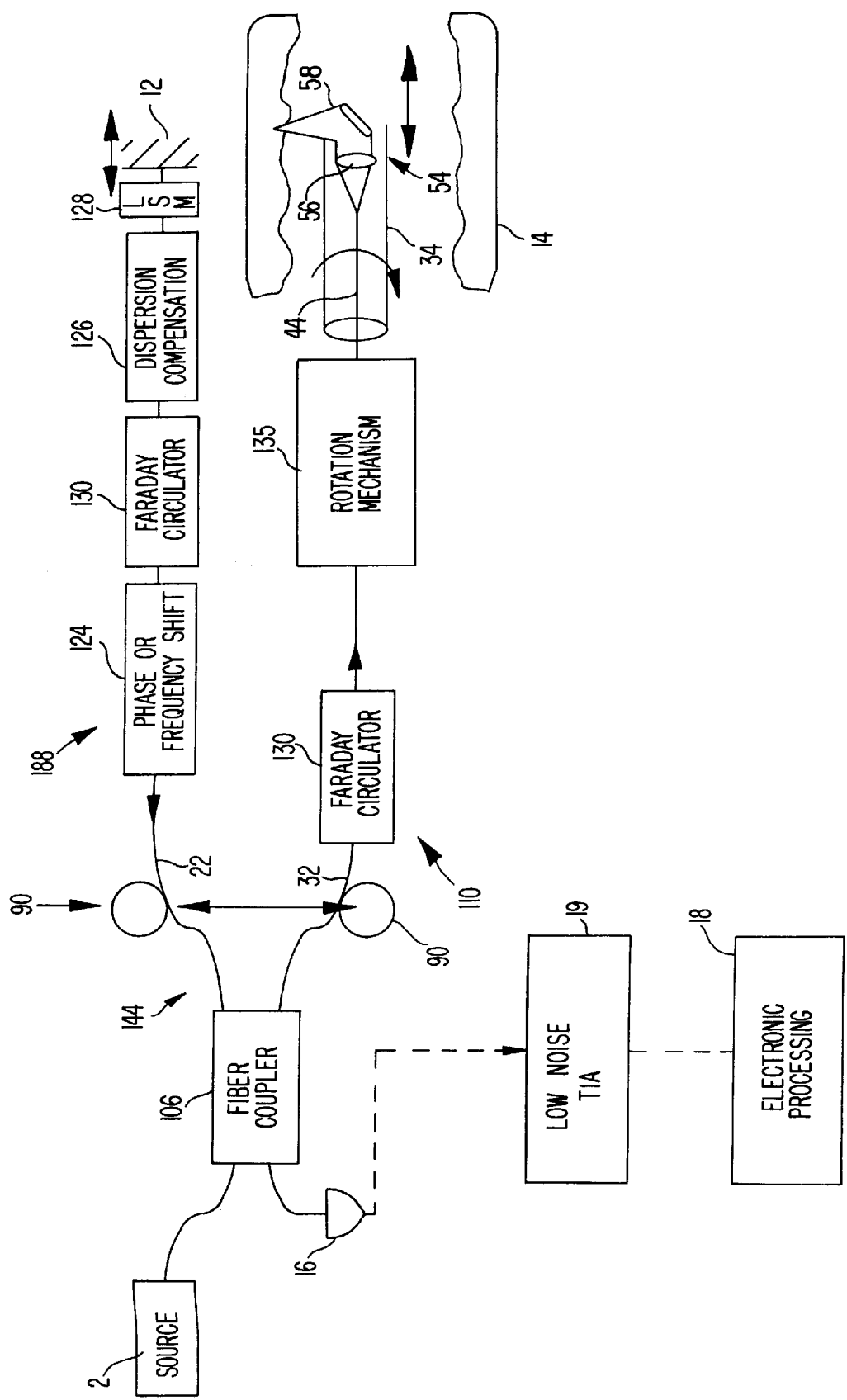
FIG. 4 depicts two embodiments of the longitudinal scanning mechanism of the present invention.

Referring to FIG. 4, the methods for performing longitudinal scanning are addressed. In order to maintain good detection sensitivity in rotational priority scanning the reference light must be frequency shifted to move the interference signal away from baseband 1/f-type noise and to prevent aliasing using serrodyne techniques with a phase shifter or an acousto-optic frequency shifter 128. In this figure, either a longitudinal scanning mechanism 128 can be used to move the reference reflector 12, or a fiber stretcher 90 can be used to change the path length. The longitudinal scanning mechanism 128 can include for example, a stepper motor, a DC servomotor, or an electromagnetic speaker coil. The length or extent of movement by the longitudinal scanning mechanism 128 is preferably at least slightly greater than the desired scanned depth range in the structure. The longitudinal scanning mechanism 128 preferably has a velocity at which it moves the reference reflector 12 that is uniform at least during the times when scanning occurs, i.e. a step function. Alternatively the velocity imparted by the longitudinal scanning mechanism 28 may take the form of a ramp or sawtooth function. A movement detector (not shown) can further be coupled to the longitudinal scanning mechanism 128 to detect the position of the reference reflector 12 in order to achieve uniform motion of the reference reflector 12 or to sense the actual velocity profile and correct for the nonuniform velocity in electronic processing unit 18. More specifically, the longitudinal scanning mechanism 128 can be coupled to a uniform motion system (not shown), capable of transmitting a signal indicative of desired position of the reference reflector 12 at each point in the travel path of the reference reflector 12 to be compared against a signal from a position detector (not shown). Any resulting error signal is then utilized to control the longitudinal scanning mechanism 128 to maintain the reference reflector 12 moving at a desired constant velocity.

Figure 5A:
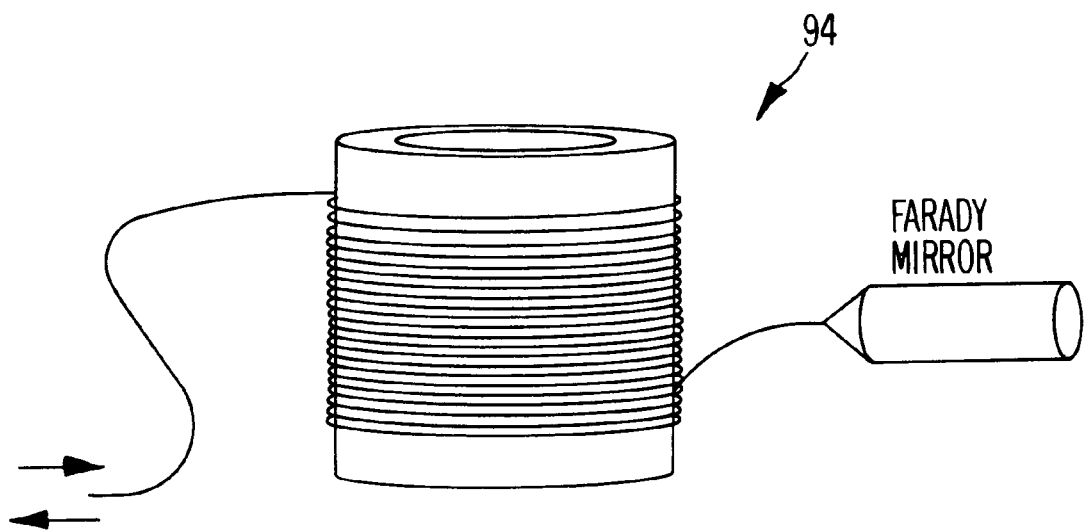
FIG. 5A depicts an embodiment of the reference reflector, particularly a helical cam for use with the imaging system of the present invention.

As shown in the embodiments of FIGS. 4 and 5A, modulation can be carried out with fast fiber stretching using two piezoelectric transducers (PZT) comprising a piezoelectric modulator-type spool around which the optical fibers are wound. As shown in this figure, both the optical fiber 22 of the reference arm 188 and the optical fiber 32 of the measuring arm 110 can thus be wound around a PZT or around another suitable form that can be expanded or contracted using actuation. Each PZT may be driven out of phase, so that as the PZTs periodically stretch the fibers 22, 32 to change the lengths of the optical paths of the reference 188 and measurement 110 arms, the scanning distance into the structure 14 is doubled. As shown, a fiber can be stretched utilizing PZT ceramics, and more particularly in this embodiment, a spool-type piezoelectric modulator 90. This approach may achieve high speeds (~1 kHz) and strokes of 5 mm.

When many meters of fiber are wrapped around a piezoelectric modulator, bending induced birefringence occurs. It is important that the wound fibers in each arm 188 and 110 be wound identically to match as closely as possible the fiber birefringence. To correct for the bending induced birefringence in both arms, a Faraday circulator 130 may be placed in the sample and reference arms after the wound fibers. Faraday circulators 130 have the property of unscrambling the polarization upon return of the light at the input. In many applications the use of a standard Faraday circulator 130 is sufficient. However, for very wide bandwidth sources, the Faraday circulator's 130 wavelength dependent polarization rotation leads to imperfect canceling of the polarization scrambling. To overcome this limitation, several practical solutions exist to correct this problem, one of which is to use wavelength independent Faraday circulators 130 (such as Ytterbium Iron Gamet, $Yb_3Fe_5O_{12}$). Additionally, a polarization maintaining or single-polarization fiber can be used. It is important that the length of the fiber in each arm 188 and 110 be substantially matched to prevent the differences in dispersion in the two optical paths from decreasing system resolution. Typically, matching lengths to about 1 mm is sufficient. In addition, to compensate for the optics used to direct and focus light from endoscopic unit 34, a dispersion compensating unit 197 can be used. Preferably, the unit 197 has an equal amount and type of glass or other material as is used in endoscopic unit 34.

Figure 5B:
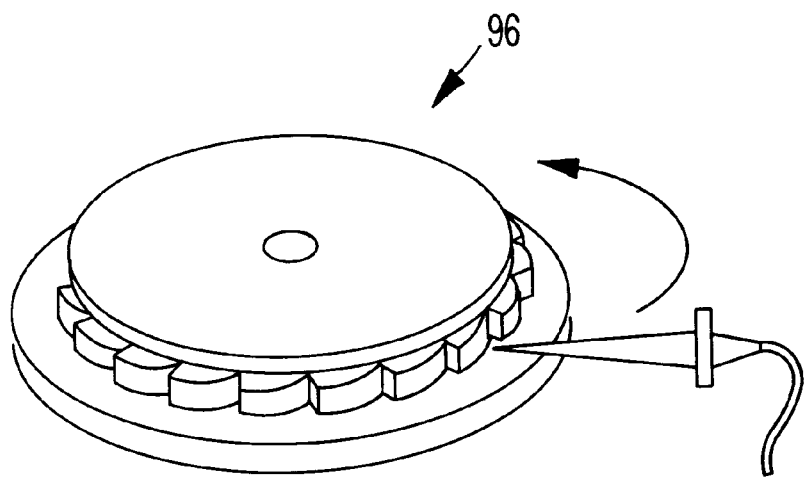
FIG. 5B depicts an embodiment of a PZT cylinder for use with the imaging system of the present invention.

Another approach to changing the length of the reference arm, is shown in FIGS. 4 and 5B. Shown in FIG. 5B is a reference reflector forming a spinning cam 96 having jagged edges. As an incident radiation beam is directed toward the edges of the cam while it is undergoing rotational motion, the jagged edges of the cam 96 result in a periodic and nearly constant velocity variation in the path length. The periodicity of the length variation is equal to the number of segments times the time for one full 360° rotation of the cam.

Endoscopic Unit

Figure 6:
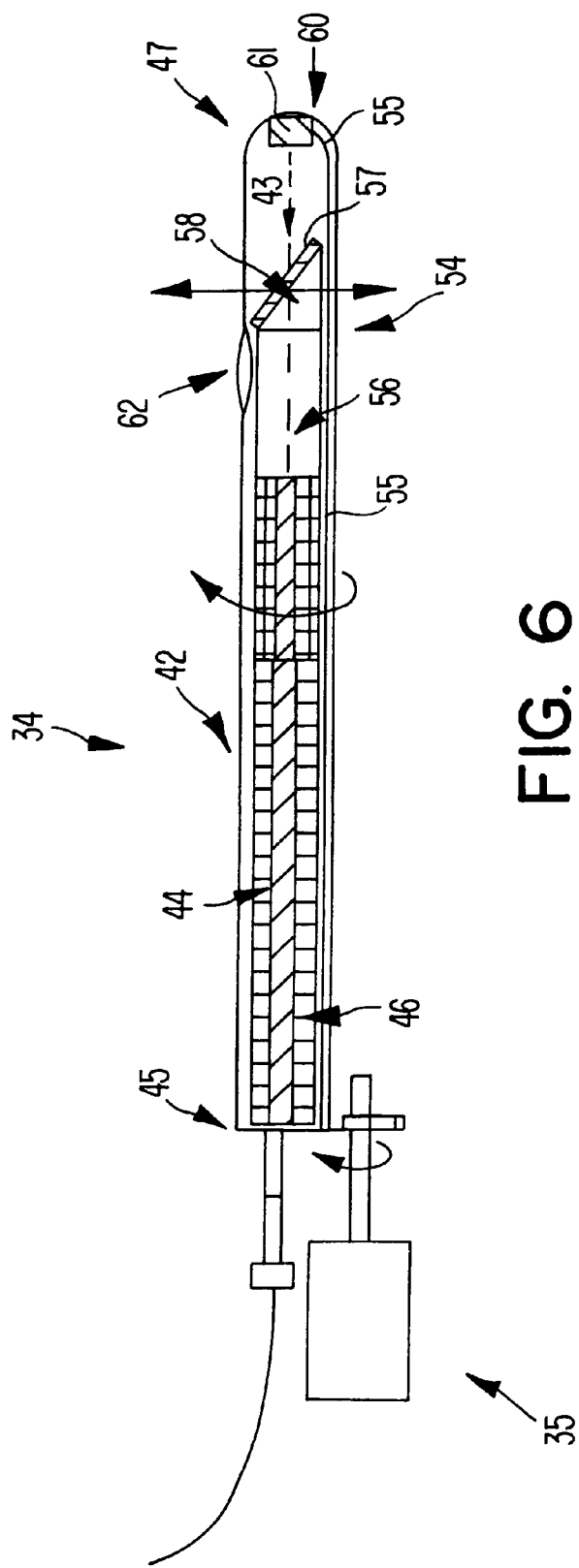
FIG. 6 depicts an embodiment of the endoscopic unit of the imaging system.

Referring to FIG. 6, shown is an embodiment of the endoscopic unit 34 coupled to a rotational scanning mechanism 35. The endoscopic unit 34 is adapted for insertion into a natural or surgically created orifice in the human body, to enable medical personnel to view a structure, such as an artery, in situ. Viewing may take place while performing an invasive procedure or for diagnostic purposes and may be used to actively control the procedure. The rotational scanning mechanism 35 imparts movement on either the optical fiber 44, as further described in FIG. 8, or a component of the optical system 54, as further described in FIG. 10, such that imaging takes place.

As shown in this embodiment, the endoscopic unit 34 generally includes a hollow housing 42 forming an elongated bore 43 having a proximal end 45 and a distal end 47. At the distal end is an optical system 54 through which optical radiation is directed toward and collected from the structure of interest. The housing 42 may include an invasive member such as serrated edge (not shown) at its distal end 47. Within the bore 43 of the housing 42 resides an optical fiber 44, which is, in one embodiment a flexible single mode optical fiber or a single mode fiberoptic bundle having standard, or polarizing maintaining, or polarizing fibers to insure good polarization mode matching. The optical fiber 44 is preferably encased in a hollow flexible shaft 46. As the endoscopic unit 34 both illuminates and collects retroreflected light the optical fiber 44 is preferably a single mode optical fiber. The use of a single mode fiber is preferable for applications of OCT imaging because it will propagate and collect a single transverse spatial mode optical beam which can be focused to its minimum spot size (the diffraction limit) for a desired application. Preferably the single mode optical fiber 44 consists of a core, a cladding, and a jacket (not shown). The radiation beam is typically guided within the glass core of the fiber 44 which is typically 5–9 microns in diameter. The core of the fiber is typically surrounded by a glass cladding (not shown) in order to both facilitate light guiding as well as to add mechanical strength to the fiber 44. The cladding of the fiber is typically 125 microns in diameter.

An irrigation port 62 is formed near the distal end 47 of the housing 42 for irrigating the structure being imaged. The rotational scanning mechanism 35 causes rotation of the optical fiber 44 or a component of an optical system 54 disposed at the distal end 47 of the optical fiber 44. The housing 42 includes a transparent window 60 formed in the area of the distal end 47 and adjacent the optical system 54 for transmitting optical radiation to the structure 14 being imaged. The rotational scanning mechanism 35 enables the optical radiation to be disposed in a circular scan. When combined with longitudinal scanning, as described above, the imaging depth of the optical radiation is changed, as further described below.

Figure 7A:
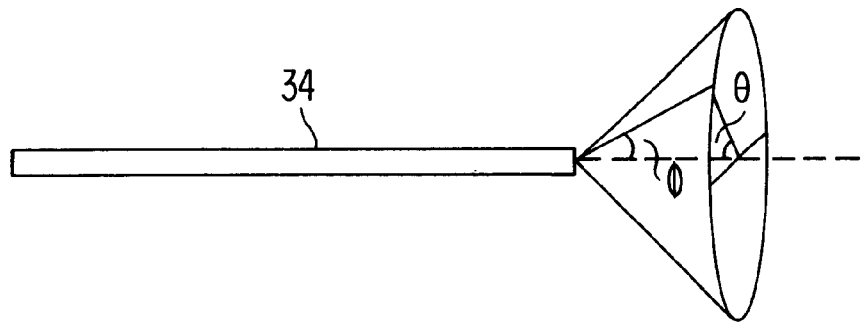
FIGS. 7A–7C show scan patterns achieved with different beam directing optics in the imaging system of the present invention.

Referring to FIG. 7A, the optical radiation beam can be emitted out of the distal end of the endoscopic unit 34 or out of the side of the endoscopic unit 34 at an angle, $\phi$, to the axis of the endoscopic unit 34. The beam emission direction is scanned rotationally by varying its angle of emission, $\phi$, along the axis of the endoscopic unit 34. The optical radiation beam can further be directed at an angle, $\phi$, which deviates from 90 degrees. This facilitates imaging slightly ahead of the distal end of the endoscopic unit 34. In this implementation, the emitted beam scans a pattern which is conical, with a conical angle of $2\phi$. When used with longitudinal scanning, this scan pattern generates a cross sectional image corresponding to a conical section through the artery or vessel or tissue, as further shown in FIG. 14. The angle $\phi$ may be adjustable, as to cam be responsive to control signals from signal processing and control electronics 18 or manually adjustable. Due to the adjustability of the angle, nearly all forward imaging, mainly transverse imaging, or backward imaging may be accomplished for example, by utilizing a component of the optical system such as a beam directing optic, a movable mirror, an electro-optic device, or alternatively by displacing the fiber in the focal plane of the lens, or displacing the lens using microrevolution devices. Rotational or axial scanning may be accomplished along the axis of the endoscopic unit 34 by varying only the angle $\phi$. This form of scanning would enable the acquisition of rotational or axial scans from within internal channels in the body, such as veins and arteries. Adjusting both $\theta$ and $\phi$, will result in the ability to perform 3-D imaging or intimal surface contour mapping. Such mapping is extremely important for some medical applications.

Figure 7B:
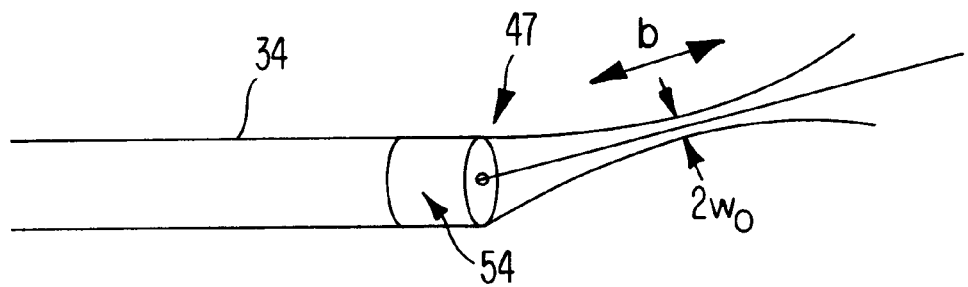

As shown in FIG. 7B, the distal end 47 of the endoscopic unit 34 may further direct the beam through a component of the optical system 54. In this figure the spot size, $w_0$, and the confocal parameter, b, for example, are optimized for a particular application. Typically, the confocal parameter b is approximately equal to the longitudinal scan range. The component, as further described in FIG. 9, may include a beam director such as a lens, microlens, lens-array, or graded index lens which controls the focusing parameters of the optical beam.

Figure 7C:
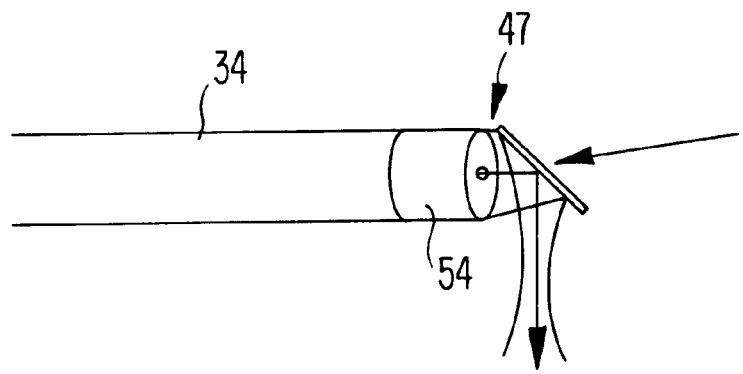

Alternatively, as shown in FIG. 7C, the optical beam may be emitted from the distal end 47 of the endoscopic unit 34 in a direction which is perpendicular to the axis of the endoscopic unit 34. As further described in FIG. 6 and FIG. 10, the optical system at the distal end 47 of the endoscopic unit 34 can include a suitable active or passive beam directing optic such as a microprism prism or mirror assembly which controls the angle φ and scans the angle of emission, θ, of the optical beam.

Figure 8:
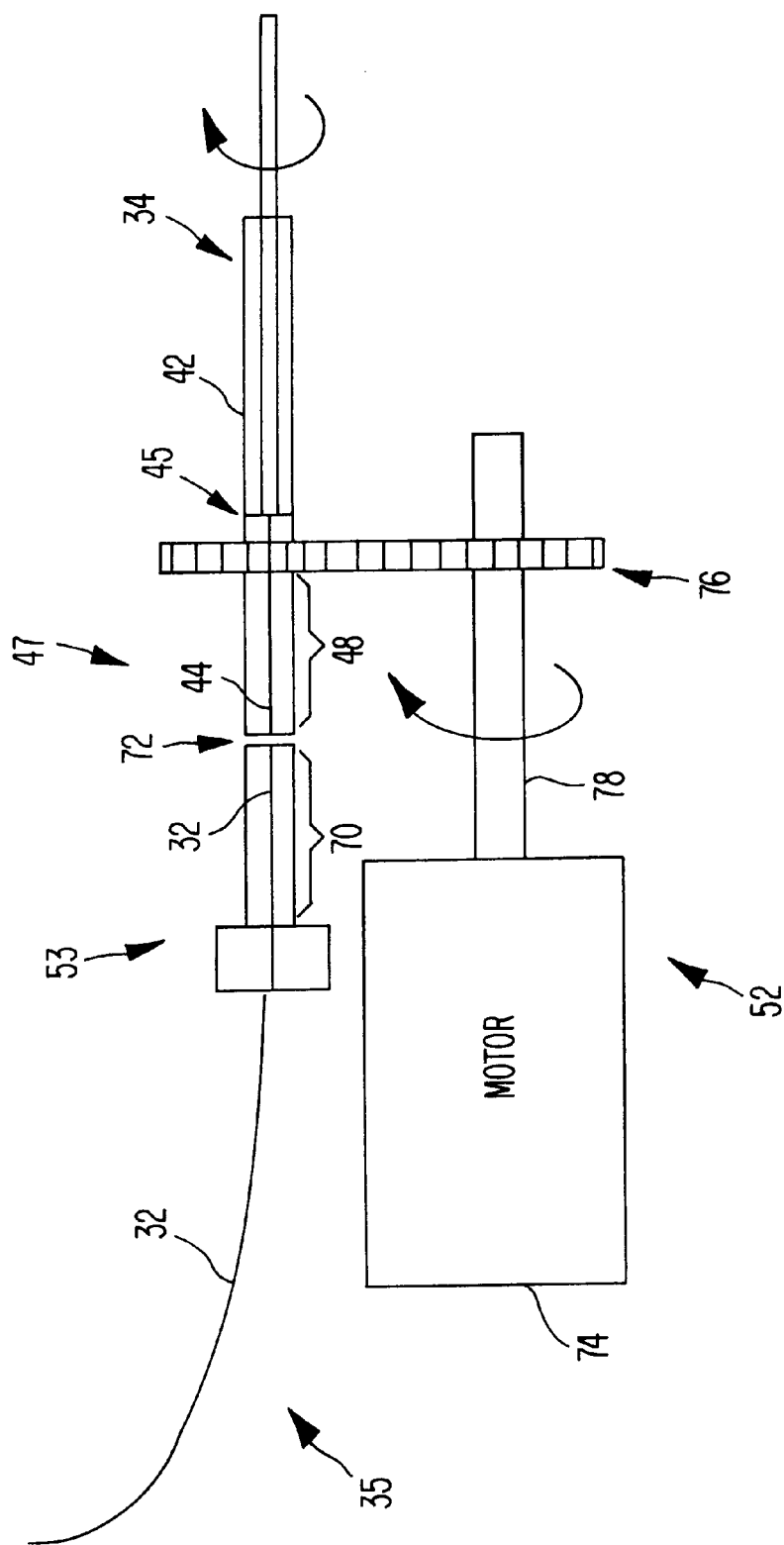
FIG. 8 depicts an embodiment of the rotational scanning mechanism associated with the endoscopic unit of the present invention.

Referring to FIG. 8 the rotational scanning mechanism 35 is described in further detail. The rotational scanning mechanism 35 typically includes a rotation mechanism 52 and an optical coupling system 53. In this figure, the optical fiber 32 that delivers radiation from the beam divider 6 terminates within the coupling system 53. The coupling system 53 includes a coupling member 70 which as shown in this embodiment, is spaced by an interface 72 from an optical connector 48 affixed to the proximal end of the endoscopic unit 34. The interface 72 is utilized to transmit optical radiation from the input optical fiber 32 to the optical fiber 44 of the endoscopic unit 34. The coupling member 70 can be physically coupled to the optical connector 48, or as shown, can be separated by an air or a fluid medium formed in the interface 72. In the event that the coupling member 70 is physically coupled to the optical connector 48, the coupling member 70 can be removed from the optical connector 48, thereby enabling the endoscopic unit 34 to be replaced with each patient. In addition to these means of coupling, additional modifications for high-speed optical imaging are possible. Either standard or gradient index (GRIN) lenses (not shown) can be used to couple light from the fixed to rotating portion of the catheter. Because more optical elements are involved, alignment of all components to the high tolerances (<1 mrad angular tolerance) are required for adequate coupling.

The optical connector 48 functions as the drive shaft for the endoscopic unit 34, as the rotation mechanism is coupled thereto. The rotation mechanism includes a DC or AC drive motor 74 and a gear mechanism 76 having predetermined gear ratios. The gear mechanism 76 is coupled to the motor 74 via a shaft 78. In all embodiments, upon activation of the drive motor 74, the shaft 78 rotates causing the gear mechanism 76 and the rotatable optical fiber 44 or a component of the optical system 54 to rotate. Alternatively, the DC drive motor 74 can be a micromotor (not shown) disposed at the distal end of housing, connected to optical system 54 causing rotation or translation of a component of the optical system 54 as further described in FIG. 10.

In embodiments where a fiber is not rotated but a component of the optical system is rotated via a flexible coupling mechanism alternative drive mechanisms to those shown in FIG. 6 and FIG. 8 are possible. Among these drive mechanisms are an "in-line" drive analogous to a drill wherein shaft 78 directly links "in line" with flexible shaft 46. A stationary sheath is used outside shaft 46 to protect fibers which are routed between the sheath and the housing 42.

The optical system 54 can include a number of different optical components depending on the type of scan desired. Referring again to the embodiment of FIG. 6, the optical system 54 includes a lens 56 and an optical beam director 58. The beam director 58 may include a lens, prism, or mirror constructed so as to minimize the effects of turbulence on the beam propagation. In this embodiment, the beam director 58 is preferably a mirror or prism affixed to a GRIN lens 56 for directing optical radiation perpendicularly to the axis of the endoscopic unit 34. The housing 42 includes a transparent window 60 formed along the wall of the endoscopic unit 34. In this embodiment the scan of FIG. 7C is achieved, as the optical radiation is directed perpendicularly through the transparent window 60 and onto the structure 14 of interest.

Referring to FIG. 6, in this embodiment, it is seen that by removing ultrasound components 61 and beam director prism or mirror element, high resolution imaging is possible if the endoscopic unit 34 has a window 160 at the tip of the endoscopic unit 34. In this embodiment the optical system includes a beam director which is a lens 156, which transmits light in a circular path as described in the scan of FIG. 7B, as the optical fiber 44 rotates. One of the many ways this can be accomplished is to position the optical fiber 44 slightly off the axis in which the lens 156 is disposed.

Figure 9:
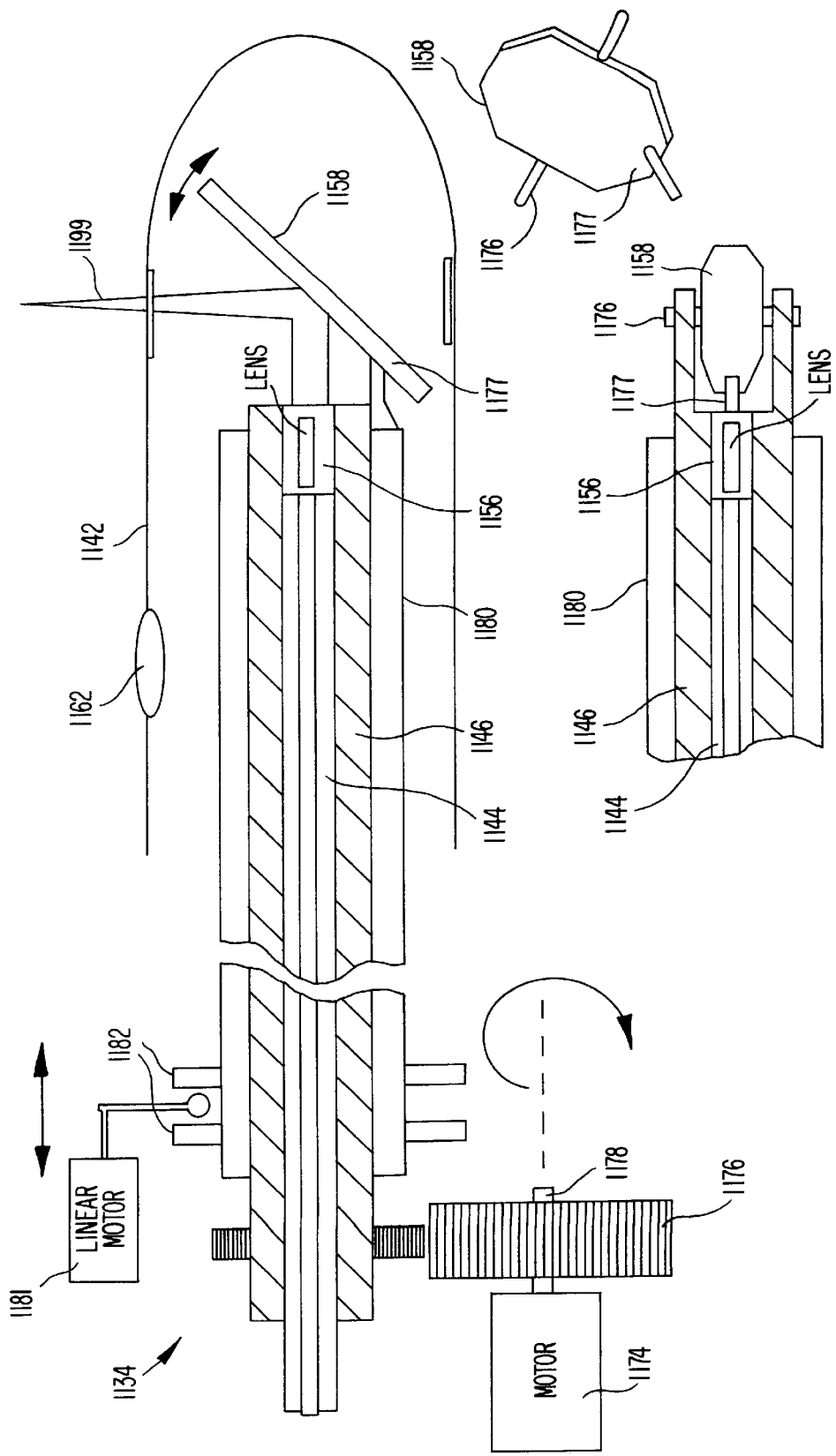
FIG. 9 depicts an embodiment of the optical system associated with the endoscopic unit of the present invention.

As previously discussed there are several methods to perform scanning in θ, φ, referred to in FIG. 7A. This includes radially displacing the distal fiber tip using miniature microtranslators (not shown) in the image plane of the lens in the optical beam directing optic 54 (FIG. 6) and mechanical or electromagnetic, or piezoelectric displacement of the fold mirror in the beam directing optic. One method based on mechanical linkage is shown in the embodiment of FIG. 9. As shown in this figure, and as was previously described, there is a fiber 1144 housed in a flexible torque cable 1146. The distal end of the torque cable is connected to a gear mechanism 1176. On of the gears is connected to shaft 1178 driven by AC or DC motor 1174 so as to produce rotational scans of the sample of interest. At the distal end of endoscopic unit 1134 is lens 1156 which serves to focus light from fiber 1144 into the sample and to collect backscattered or backreflected light from the sample and deliver it to the fiber 1144. In this embodiment of the invention an outer sheath or cable 1180 is torsionally tightly coupled to flexible cable 1146 using ribbed sleeve (not shown) or grooves (not shown) in sheath 1180. Although the sheath 1180 is tightly torsionally coupled, it is allowed to slide axially and is driven by linear motor 1181 with suitable coupling means to two plates 1182 affixed to the sheath 1180. Thus, as the motor 1174 drives torque cable 1146 in rotation, the linear motor 1181 can drive the sheath 1180 axially. At the distal end of the endoscopic unit is a mirror beam directing optic 1158. This mirror is hinged in two ways. One hinge 1176 is connected to torque cable 1146 in a torsionally stiff way to drive the mirror in rotation. Another single hinge point 1177 is connected to sheath 1180 so as to drive the mirror in tip and tilt in response to motor 1181. Housing 1142 is suitably metered off of sheath 1180 so as to protect mirror 1177 from contacting the outer the housing 1142. In another embodiment sheath 1180 is directly affixed to torque cable 1146 and the mirror 1158 is replaced with prism beam director attached directly to lens 1156. Gearing mechanism is suitably made to allow motor 1181 to axially drive the entire endoscopic imaging unit in the axial direction. These example embodiments enable beam 1199 to perform automated three dimensional maps of the sample of interest.

Figure 10:
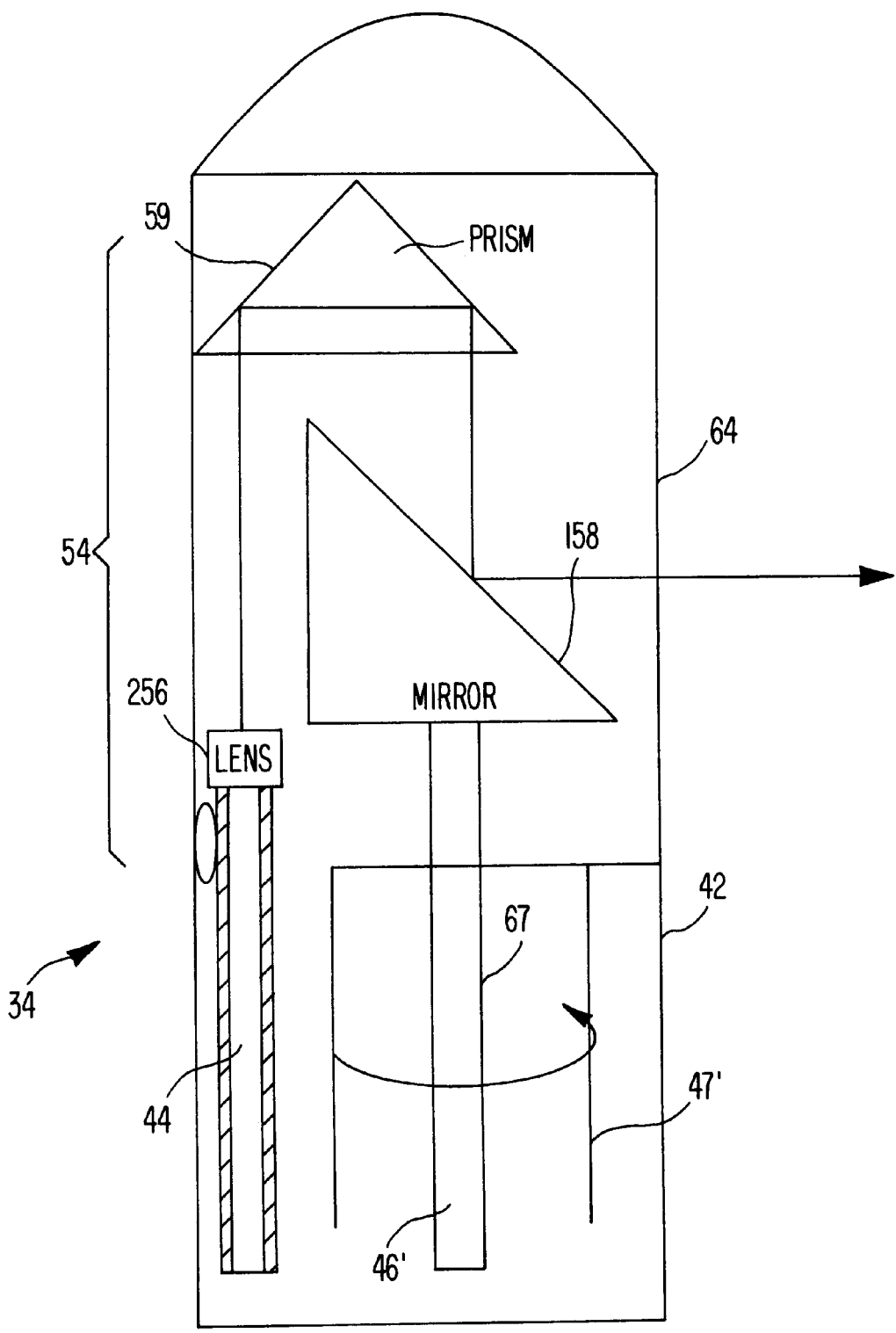
FIG. 10 depicts an alternate embodiment of the optical system associated with the endoscopic unit of the present invention.

Another alternative embodiment of the endoscopic unit 34 of the present invention is shown in FIG. 10. In this embodiment, the optical system 54 preferably comprises a lens 256, a retroreflector such as a prism 59, and a beam director 158 such as a mirror. In this embodiment the transparent window 64 is located circumferentially around the wall of the housing 42 to reflect radiation out the side of the endoscopic unit 34. In this embodiment neither the optical fiber 44 does not rotate to create a circulation radiation scan. Instead, the beam director 158 is connected to a flexible rotatable shaft 46' which is connected to the reducing gear 76, or to a direct "in line" linkage, similar to that previously described. Shaft 46' may be housed within protective sheath 47'. The fiber is not connected as in FIG. 6 along the axis but rather is run outside the sheath 47' and outer casing 42 toward the proximal end 45 where it is coupled to interferometer 4. This approach has the added advantage that several optical fibers may be coupled to endoscopic unit 34 and located in the image plane of lens (or lens array) 256 so as to produce several axial or rotational beams that can be scanned and acquired in parallel. In one embodiment each fiber is coupled to a separate imaging system. In another embodiment, the beam director 158 is rotated by micromotors (not shown) resident within the endoscopic unit 34.

In operation, optical radiation travels through the optical fiber 44, the lens 256, and the retroreflector 59 to the beam director 158. As the beam director 158 rotates, the radiation is reflected perpendicularly to the endoscopic unit through the transparent window 64 on the walls of the endoscopic unit 34 and onto the structure 14 in a circular fashion, as described in the path of FIG. 7C.

Referring to FIG. 11A, an alternative embodiment of the endoscopic unit 34 of the present invention includes a plurality of inflatable balloons 80 disposed adjacent the housing (not shown). The balloons 80 are inflated with fluid such as air or liquid through a lumen 81 in the endoscopic unit 34. Such balloons 80 are frequently used to destroy plaque or isolate an area within an artery. As shown in this figure, in one embodiment at least one balloon 80 can be transparent and disposed over a transparent window 64. Because the balloon 80 is transparent, the radiation from the single mode optical fiber 44 is transmitted through the optical system 54 and the balloon 80 to the structure. With such an arrangement, the effect of the balloon 80 on plaque may be imaged as the angioplasty is occurring. If a micrometer or other suitable means is attached to alter the angle Φ in FIG. 7C, then the axial image of the balloon can be mapped out with the rotational mapping, thereby creating a 3D image. As also shown in this figure, a guidewire 82 may be included with the housing 42 of the endoscopic unit 34. The guidewire 82 facilitates in positioning the endoscopic unit 34 at a desired location in the body.

Imaging from within this angioplasty endoscopic unit 34, will allow real-time assessment of vessel or tissue wall before, during, and after balloon inflations. This will allow balloon 80 dilatation pressures to be adjusted until the desired results are achieved. Currently, a pressure is estimated prior to the procedures based on gross criteria and the pressure is changed if the angiogram post procedure does not suggest substantial improvement. The angiogram is low resolution (greater than 500 μm) and assesses the vessel or tissue in an axial rather than cross sectional manner. In applications where blood flow causes degraded imaging, the upstream balloon can be inflated and/or saline injected to clear the optical imaging field. Inflation of the balloon nearest the optical imaging port also can be used to stabilize the imaging field.

Referring to FIG. 11B, shown is the endoscopic unit 34 of FIG. 11A, in cross section. As shown, fiber 44 runs through the center of the housing, enclosed by a flexible torque cable 45 and a body 47. Formed within the body 47 are inflation ports 81, through which balloons 80 are inflated. Additionally a port 49 is defined in the body 47 through which the guidewire passes 82. Preferably a biocompatible sheath 84 is disposed on the outer surface of the body 47. Additional a lumen 89 can be used to inject or extrude fluids such as saline.

Figure 12:
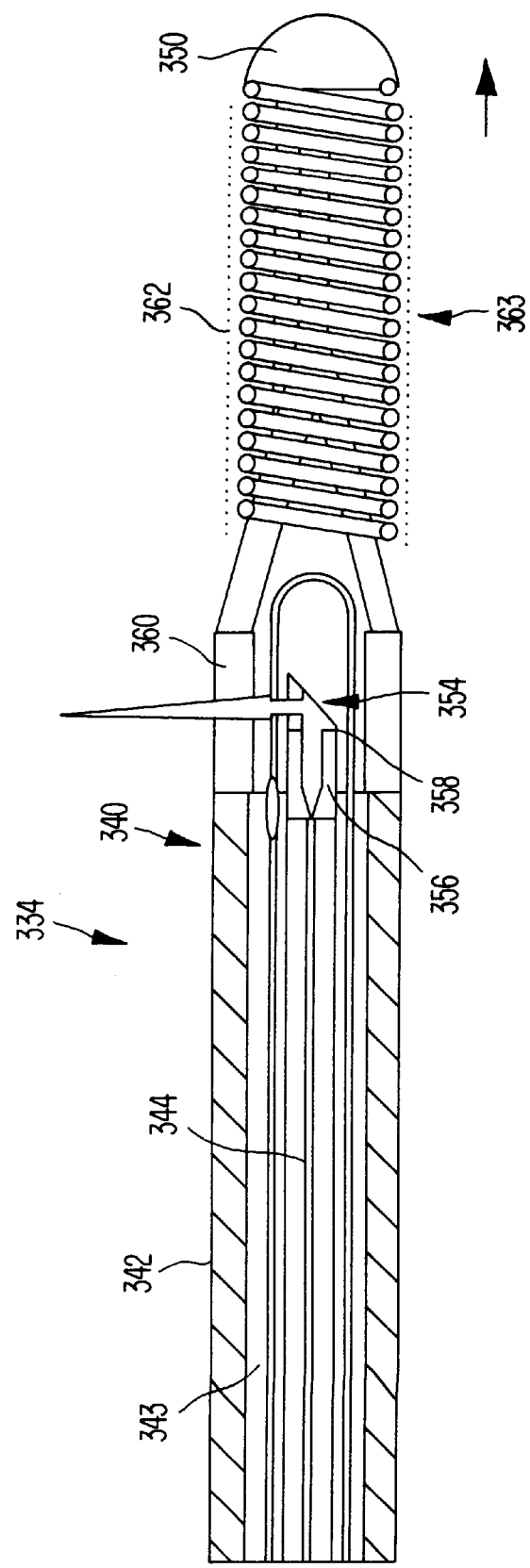
FIG. 12 depicts an alternate embodiment of the endoscopic unit of the present invention which includes a guidewire.

Referring to FIG. 12, shown is another embodiment of the imaging system that includes a guidewire 334 to direct a catheter or endoscope through an artery or vein. The guidewire 334 generally comprises a housing 342, forming a hollow elongated bore 343 within which, as similarly described above, a rotating optical fiber 344 extends. Formed at the distal end of the guidewire 334 is a flexible tip 363 preferably fabricated from a coiled biocompatible radiopaque material with a radiopaque tip 350. The flexible tip 363 typically extends approximately 4 cm beyond window 360 and may be covered with a smooth jacket 362. An optical system 354 is preferably positioned at a stationary area 340 in the guidewire, as the moving tip 350 may make it difficult to obtain images or the presence of optics will reduce the flexibility of the tip. However, the optical system, in another embodiment can be formed at the tip (not shown) if desirable to the user's intended application. In another embodiment, the apparatus of FIG. 9 may be located at the end of the guidewire 334. In many applications is may only be necessary to perform one-dimensional longitudinal scanning at the tip of the guidewire to aid in placing the guidewire in the body. As such it is only necessary to place one stationary fiber in the flexible tip. 350. This position of the optical system 354 will allow interventional catheters to be switched over the wire while imaging is continuously performed. The optical radiation from the optical fiber 344 is transmitted to the optical system 354 where it is transmitted, in this embodiment, through a lens 356 and a beam director 358 and through the window 360.

There are several methods in which the window 360 is formed while still maintaining structural integrity of the guidewire 334. One method involves using three or more metal or plastic metering rods that attach the flexible tip 350 to the stationary area 340 of the guidewire. Another method involves using a rigid clear plastic widow that may to sealed to the metal or plastic guide wire at the distal and proximal sides of the window. Alternatively, the hollow flexible shaft housing the rotating fiber 344 may be attached to the inside of the metal guidewire housing 334 or may be left freely floating in the bore 343 of the guidewire 334.

Referring again to FIG. 6, in an alternate embodiment of the invention, the imaging system can be coupled with an ultrasonic system. As shown in this figure, an ultrasonic transducer 61 is located within the housing at the distal tip. The beam director 58 is preferably a prism or mirror having a silvered edge 57 through which optical radiation is transmitted perpendicularly to the structure 14 of interest, as described above. The ultrasonic transducer 61 transmits ultrasonic waves to the silvered edge 57, causing perpendicular impingement on the structure in the direction opposite that of the optical radiation. A lead wire 55 emanates away from the transducer, delivering detected ultrasonic signals to a processing unit (not shown).

Figure 13:
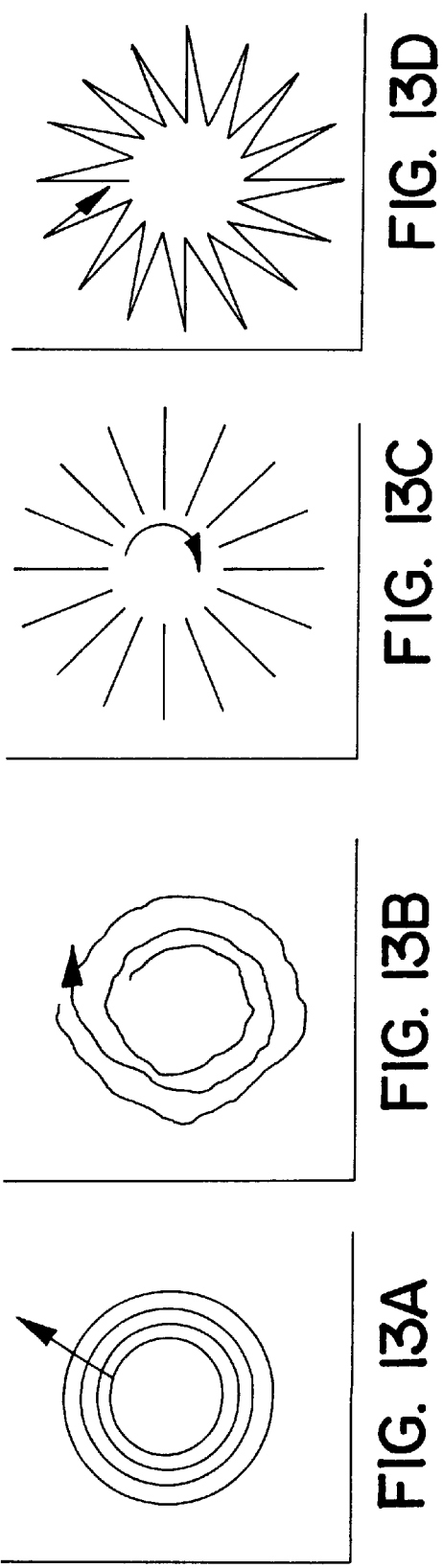
FIG. 13A–FIG. 13D depicts various combinations of rotational and longitudinal scans performed by the imaging system of the present invention.

Referring to FIGS. 13A–13D, shown are examples of two types of scanning approaches of internal body organs. The priority for scanning can be such that longitudinal scanning is interlaced with rotational scanning. Rotational priority scanning is shown in FIG. 13A. In this figure, one rotational scan is substantially completed before longitudinal scanning takes place. As a result, the successive circular scans provide images of successive depth within the structure of interest. This is performed in a discrete fashion in FIG. 13A. Referring to FIG. 13B longitudinal scanning occurs concurrently with rotational scanning. In this manner both scans are synchronized to provide a spiral scan pattern. Longitudinal priority scanning is shown in FIG. 13C. In this figure, one longitudinal scan into the tissue wall is completed before incrementing the rotational scan location. Referring to FIG. 13D, one longitudinal scan is completed as synchronized rotational scanning takes place.

Figure 14:
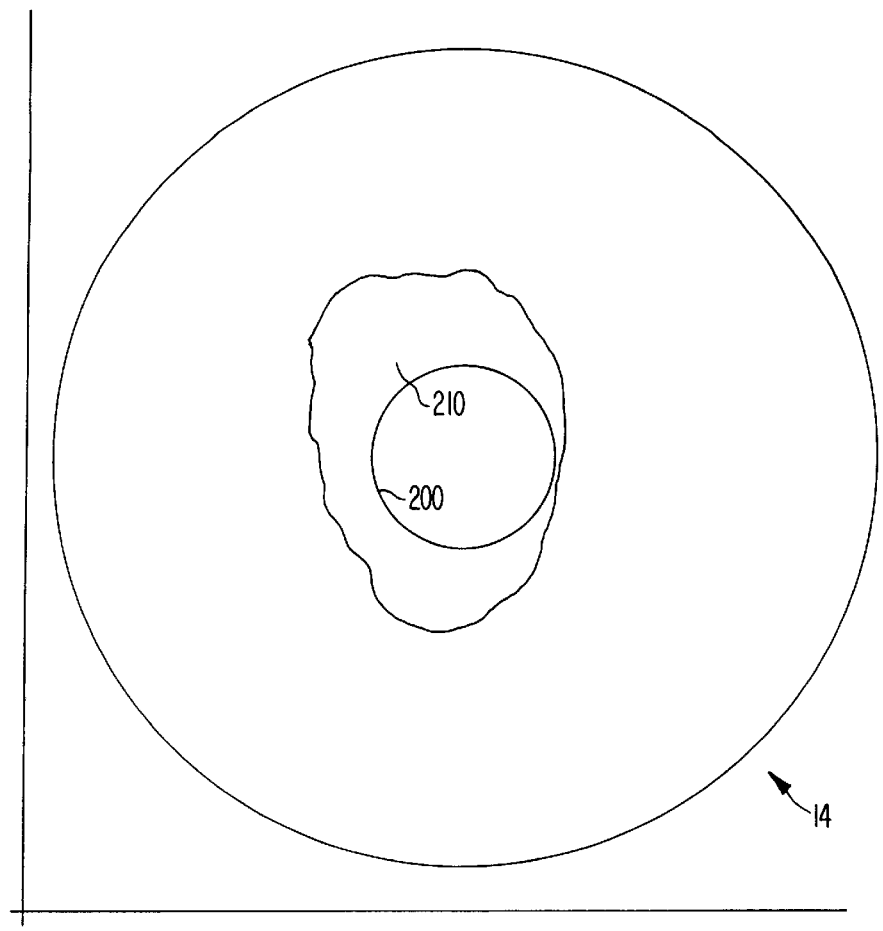
FIG. 14 depicts an image of the internal structure of an artery obtained with the imaging system of the present invention.

Referring to FIG. 14, shown is an image of a vessel obtained using the system of the present invention. As shown by reference numeral 200 and 210, both the surface of the structure 14 as well as the internal features of the structure 14 can be obtained with the rotational scans performed by the components of the measuring arm 10, and the longitudinal scans performed by the components of the reference arm 8.

Loss Compensation Embodiments

In any of the above-noted embodiments, in order to increase or maintain the signal to noise ratio and resolution compensation for dispersion and polarization losses must be carried out. Referring again to FIG. 4, the optical path defining the reference arm 188 includes an optical fiber 22 optically coupled with a phase and/or frequency shifter 124, and a dispersion compensation system 126. In longitudinal scanning demodulation of the interferometric signal in processing unit 18 takes place at an intermediate frequency equal to or near the Doppler frequency of longitudinal scanning unit 12. However, in rotational scanning, a suitable means to shift the intermediate frequency is needed. The phase and or frequency shifter 124 performs this function.

The phase and/or frequency shifter 124 maintains optimal detection sensitivity by modulating the frequency of the interference signal component of the radiation away from baseband-type noise and prevents aliasing. The phase and/or frequency shifter 124 can, for example, take the form of a phase modulator with serrodyne modulation, such as an $LiNbO_3$ electrooptic modulator or a stretchable fiber. Serrodyne phase modulation is effectively accomplished by using a saw tooth drive pattern with an amplitude that is reset at multiples of $2\pi$. Alternatively, the phase and/or frequency shifter 124 can be an acousto-optical modulator. The frequency shift required is approximately several times the rotational impulse response. The impulse response has the duration T~(rotational velocity)/(focal-spot size). The nominal bandwidth used in the electronic processing unit is set to be approximately equal to the rotational pulsewidth in rotation scanning or the longitudinal pulse width (coherence length). In longitudinal scanning the filter center frequency is set by the serrodyne or the acousto-optic frequency shift or by the Doppler frequency shift for rotational or longitudinal scanning respectively. In some applications it may be necessary to have phase and/or frequency shifter 114 in both reference arms to balance dispersion or to operate at the difference frequency between the two frequency shifters.

Typically a non-fiber interferometer wavepacket will retain its shape as it travels to the reference reflector 12 and back. However, in a fiberoptic interferometer 144 as shown in FIG. 4, the fiber material, waveguide dispersion, bulk optical components and the tissue dispersions will cause the various frequency components of the wavepacket of the optical source 2 to travel at different speeds, in effect smearing out the wavepacket and decreasing resolution of imaging. In applications where high peak power pulses are used, self phase modulation can also cause detrimental effects on resolution. To maintain dispersion balancing, identical lengths of fibers in each arm 188, 110 and/or dispersion balancing components 126 can be used. The dispersion compensation system 126 equalizes (to less than the coherence length) the difference in the dispersion of the radiation reflected in the reference arm 188 and measurement arm 110 caused by differences in the path lengths. As shown in this figure, the fiber path lengths from the coupler 106 to the reflector 12 should be approximately equal to the path length from the coupler 106 to the distal end of the endoscopic unit 34. In addition to matching the length of fiber to less than a dispersion length, the dispersion compensation system 126 may include optical elements (not shown) comprising glass to compensate for the nominal dispersion incurred as the light exits the fiber in the endoscopic unit 34, and is guided by optical elements 54 and reflects off of the structure 14 of interest, and reenters the endoscopic unit 34. In all embodiments it is important to minimize stray reflections by using anti-reflective coated optics 56 (or optical unit 54) and fibers 22, 32, 44 as well as angle polished open-ended fibers or fiber connectors (not shown). It is further desirable to separate the reference and signal fiber lengths and connector locations by a few coherence lengths so that there are no coherence interactions from these residual reflections.

Further interferometric detection requires alignment of the reference and signal polarization vectors to maintain polarization sensitivity. If the optical fiber 44 of the measuring arm 110 is moved or heated, or if the structure 14 of interest is birefringent, then signal fading can occur. Polarization preserving fibers or polarizing fibers are one solution to this problem of fiber movement or heating, although they do not compensate for birefringence of the structure 14. In addition, the fibers typically do not precisely maintain polarization, the result of which is a smearing out of the coherence function or loss of signal. The use of a polarization diversity receivers 416 as shown in FIG. 15 compensates for both polarization problems.

Figure 15:
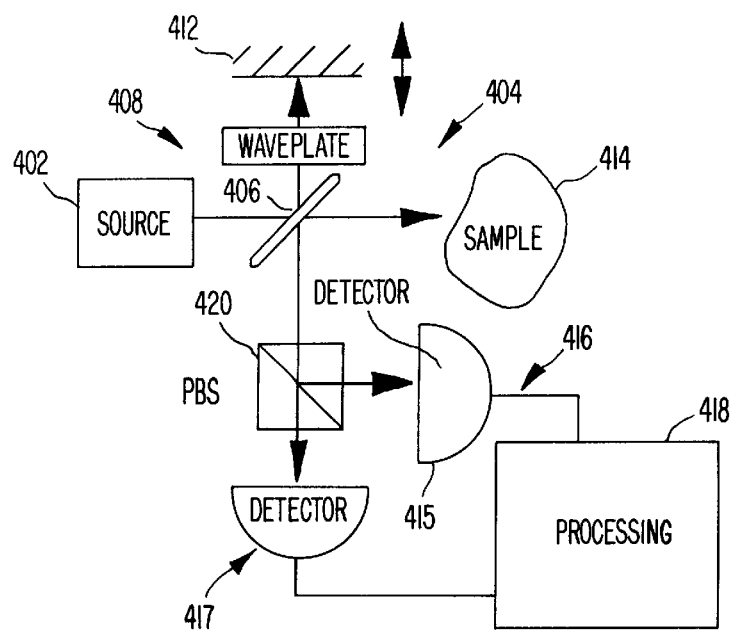
FIG. 15 depicts an embodiment of an interferometer of the present invention including a polarization diversity receiver.

Referring to FIG. 15, shown is an embodiment of the interferometer 404 including a polarization diversity receiver 416. Such a receiver 416 employs two polarization diversity detectors 417, 415. Optical radiation reflected from the reference reflector 412 and reflected from the structure 414 under observation are combined by the beam splitter 406, which may comprise an optical coupler in an optical fiber embodiment of the interferometer. Using polarization controllers (not shown) the reference arm 408 polarization is adjusted so as to equally illuminate the two detectors 417, 415 using a polarization beam splitter (PBS) 420. In an embodiment in which this portion of the optical path is in open air, a bulk zero-order waveplate between beamsplitter 406 and reference reflector 412, or other suitable location, can be used. In an embodiment in which an optical fiber is used for this portion of the path, a fiber polarization rotation device (not shown) may be utilized.

Using this receiver 416 configuration of FIG. 15, the sum of the squared outputs of the two photodetectors 417, 415 will be independent of the state of polarization of the reflected light from the structure 412. The use of such a receiver 416 can eliminate signal fading due to polarization rotation within the structure 414 and can provide information about the birefringence of the structure 412 by examining the relative strengths of the two polarization components. The sum of the squared outputs of the two detectors 417, 415 will be independent of the state of polarization of the light reflected from the structure 412. As the interferometric signal in one detector 417 is proportional to the sample electric field in the horizontal polarization, and the signal in the other detector 415 is proportional to the sample electric field in the vertical polarization, the sum of the square of these two electric field components is equal to the total power. It is possible to extend this polarization diversity receiver to a polarization receiver by using additional detectors and waveplates so that the entire stokes parameters or poincare sphere is mapped out on a scale equal to the coherence length as is known to those of ordinary skill.

As stated above, single-mode fibers are typically used to couple light to and from the structure 14. Additionally, a bulk optic probe module, such as a lens is used in the endoscopic unit 34 to couple light to and from the structure 14. Often there exists a tradeoff between longitudinal scanning range (depth-of-field) and rotational resolution as is the case with conventional microscopes. The rotational resolution is proportional to 1/F# and the depth of field is proportional to $(1/F\#)^2$ where F# is the F-number of the imaging system. Thus, achieving high rotational resolution comes at the expense of scanning depth. Referring again to FIG. 7B, for a Gaussian beam the full width half medium (FWHM) confocal distance b, is approximately given by $2\pi\omega_o^2/\lambda$, where $\omega_o$ is the $e^{-2}$ beam intensity waist radius, and $\lambda$ is the source wavelength. Thus, $\omega_o$, is very small to maintain good rotational and axial resolution. The imaging depth is also small because light collected outside the confocal distance b (or depth of focus) will not be efficiently coupled back into the optical fiber. For a 20 $\mu$m rotational resolution the depth of field is ~800 $\mu$m at a wavelength of 0.8 $\mu$m. Therefore, in one embodiment it is preferred that the optical depth-of-field approximately match the longitudinal range. With the large dynamic range of OCT one can scan beyond the confocal distance and electronically equalize the signal according to the longitudinal point-spread function up to the point where signal to noise or signal to blindness limits the equalization.

Referring again to FIG. 4, the detector 16 and signal processing electronics 18 are preferably configured to provide high sensitivity and high dynamic range. One limit to the sensitivity of the system is dictated by quantum mechanical effects in the detectors. The minimum resolvable reflection from the structure 14 is given by $R_{min} \sim 3.5(v/\Delta L)/(\eta P_s/h\nu)$, where v is the longitudinal velocity of the reference mirror, $\Delta L$ is the source coherence length, $\eta$ is the detector quantum efficiency, $P_s$ is the incident source signal power, h is Planks constant, and $\nu$ is the optical frequency. Thus if the structure is rapidly scanned, v is large, then a large signal power is needed to maintain a given receiver-sensitivity. To achieve this sensitivity, a low noise transimpedance amplifier (TIA) 19 and sufficient reference signal power is required so that the shot-noise from the reference arm power dominates the thermal noise of the TIA 19.

Additionally, in one embodiment, the signal processing electronics can use phase sensitive detection techniques and inverse scattering theory or bandwidth expansion techniques to extract enhanced resolution and other additional signal information. One method to enable phase sensitive detection is for the electronic processing unit to consist of an antialiasing low pass filter followed by an A/D converter. The A/D is preferably a 12–16 bit device running at about twice the intermediate frequency.

In one embodiment the signal processing electronics 18 may further extract velocity data from the received signal. By analyzing the Doppler frequency this embodiment can obtain information on the velocity of the structure with a spatial resolution equal to the coherence length. Such a technique is an important tool for analyzing blood or bodily fluid (secretions) flow, pulse rate, etc. A digital signal processing unit (DSP) unit (not shown) can perform the frequency analysis in several ways including implementing a bank of bandpass filters around the nominal zero Doppler frequency signal.

In order to obtain higher resolution images, high speed imaging is required, necessitating high speed scanning and high power sources. However, in many instances the achievable image speed is not sufficient to eliminate motion artifacts. Although the inflatable balloons described earlier can be used to stabilize the image field, electronic image stabilization is also important. In many applications, the speed at which an individual frame can be obtained (>1 Hz) will be sufficient to minimize most motion induced artifacts. However, as OCT can have <10 $\mu$m class resolution, frame to frame stabilization will be critical to enable high resolution visualization. To provide frame-to-frame stabilization imaging processing is required. One technique is to perform two dimensional spatial cross correlation with an image or set of images defined as a reference. After calculating the peak cross-correlation vector, this vector can be applied to reregister the image thereby eliminating the motion induced artifacts. It is not necessary to search over the entire image space for the peak cross-correlation as the frame-to-frame motion is typically bounded to much less than the entire image. Additionally, the reference image may be a time varying quantity for instance, an exponential weighting of the last N frames. Also, this frame-by-frame stabilization may be linked to the sensor sensing the axial motion of the guidewire, catheter, or endoscope, thereby signaling the need for new reference frame. Other frame-by-frame stabilization techniques can be used as is known in the art.

Figure 16:
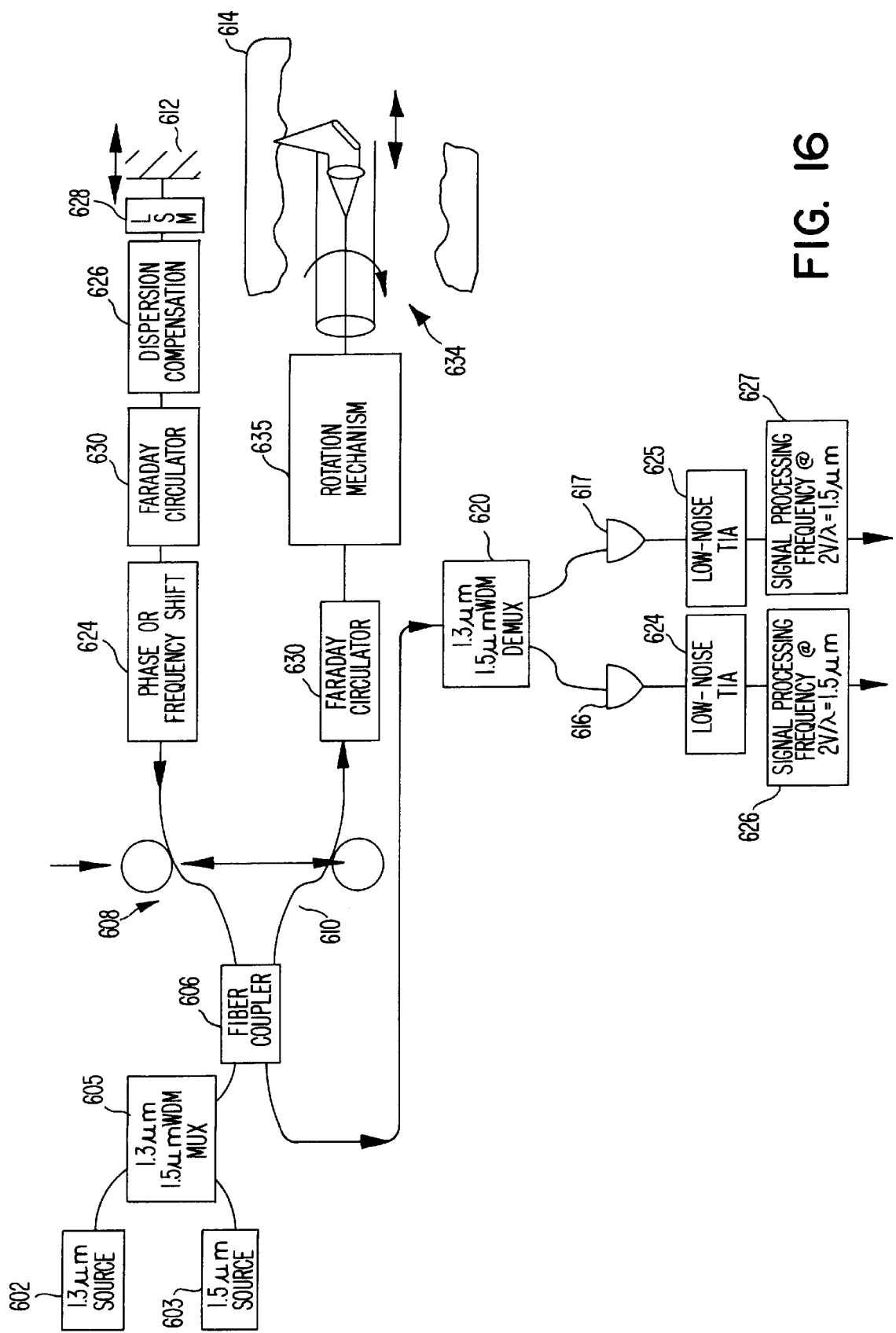
FIG. 16 depicts an embodiment of the imaging system of the present invention, utilizing wave division multiplexing.

Another embodiment of the present invention utilizes multiple optical sources tuned to different frequencies to enhance imaging of differing tissues in a structure. Referring to FIG. 16, shown is an embodiment of the present invention using wave division multiplexing (WDM). In this embodiment, two optical radiation sources 602, 603 are utilized. In one embodiment, preferably a 1.3 um source and a 1.5 um source are used. Although this embodiment shows a 1.3 $\mu$m and a 1.5 $\mu$m source, this concept can be extended to a arbitrary number of optical sources at arbitrary wavelengths. The radiation emitted by these sources 602, 603 are combined in a WDM multiplexer 605 and transmitted to a wavelength independent optical coupler 606 which, as described previously, directs the radiation along an optical path defining the measuring arm 610 including a Faraday circulator 630 and a rotation mechanism 635 coupled to an endoscopic unit 634, and along an optical path defining the reference arm 608, including a phase modulator 624, a Faraday circulator 630, and a dispersion compensation system 626. Light reflected by the reference reflector 612 and structure 614 is combined by the coupler 606 and transmitted to a WDM demultiplexer 620. The output optical signals are input optical signals to detectors 616, 617. The output signals from the detectors 616, 617 are each conditioned by a low noise transimpedance amplifier 624, 625 prior to being the input signals to one of the two signal processing modules 626, 627. The output signals from the signal processing modules 626, 627 are then processed. Thus, two simultaneous images at distinct optical frequencies can be obtained.

The two images obtained from the imaging system of this embodiment can be viewed separately or ratiometric measurements can be made to determine spectroscopic information about the structure 14. For example, radiation emitted at 1.5 um is more water-absorbing than radiation emitted at 1.3 um. By taking a ratio of images obtained with the 1.5 um source and the 1.3 um source, the water content of the sample can be determined on a microstructural scale.

As stated above, the application of WDM can enhance the ability to visualize tissue. There are several methods to wavelength multiplex signals in this invention. As shown, a singlemode fiber optic WDM multiplexer 605 for multiplexing multiple optical sources, and WDM demultiplexer 620 for demultiplexing the receiver signals can be utilized. The coupler 606 can be of the fused biconical tapered couplers or bulk interference filter type as is known to be widely commercially available. The only requirement is that the optical fibers used be single-mode over all the wavelength ranges of interest. For the demultiplexing operation, in the embodiment shown, the demultiplexer 620 is coupled to two separate detectors 616, 617. This configuration provides enhanced sensitivity as there is detected shot noise from only one optical wavelength. An alternative demultiplexer embodiment involves using a single detector (not shown) for separating the signals based on their unique Doppler shift (in longitudinal priority scanning embodiments), or serrodyne frequency shift (in rotational scanning).

Non-longitudinal Scanning Embodiments

Figure 17:
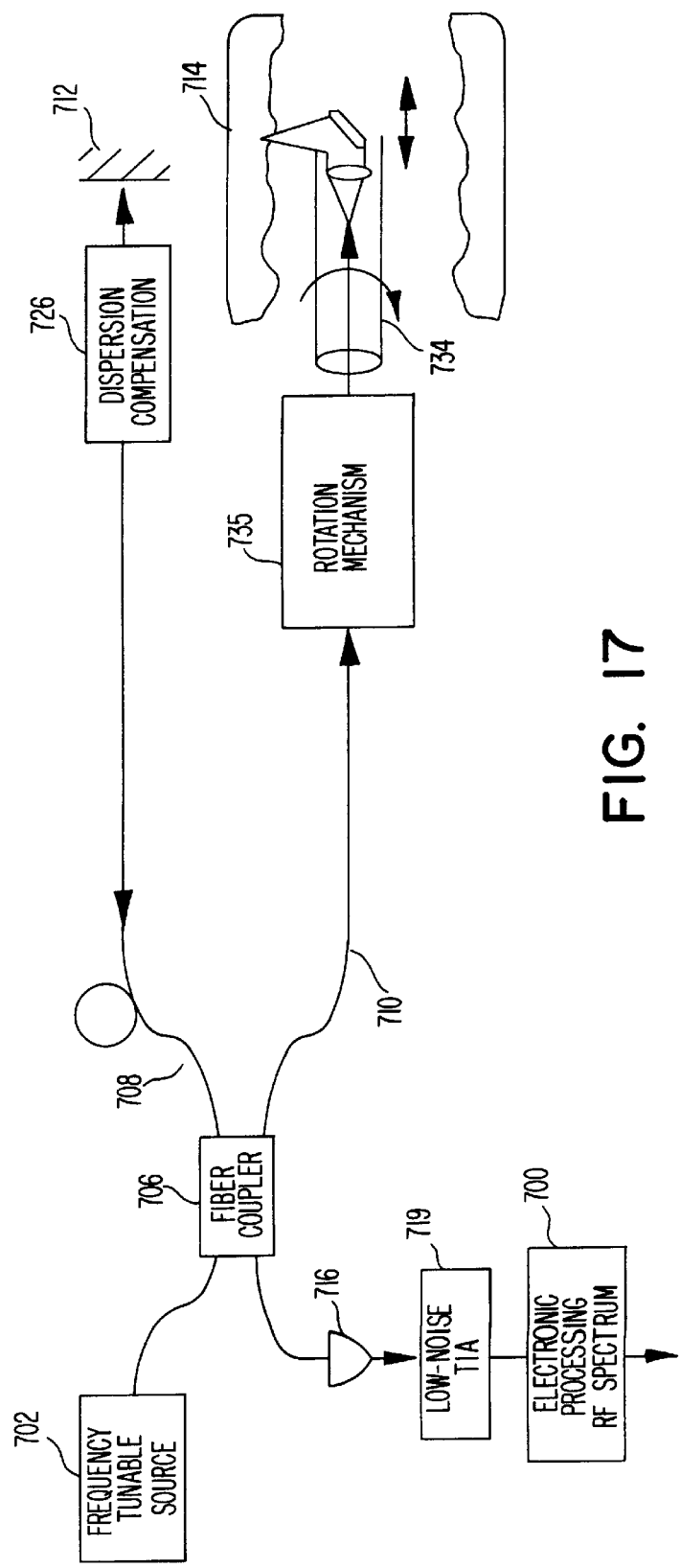
FIG. 17 depicts a non-longitudinal scanning embodiment of the imaging system of the present invention, utilizing a narrow bandwidth, frequency tunable optical source.
Figure 18:
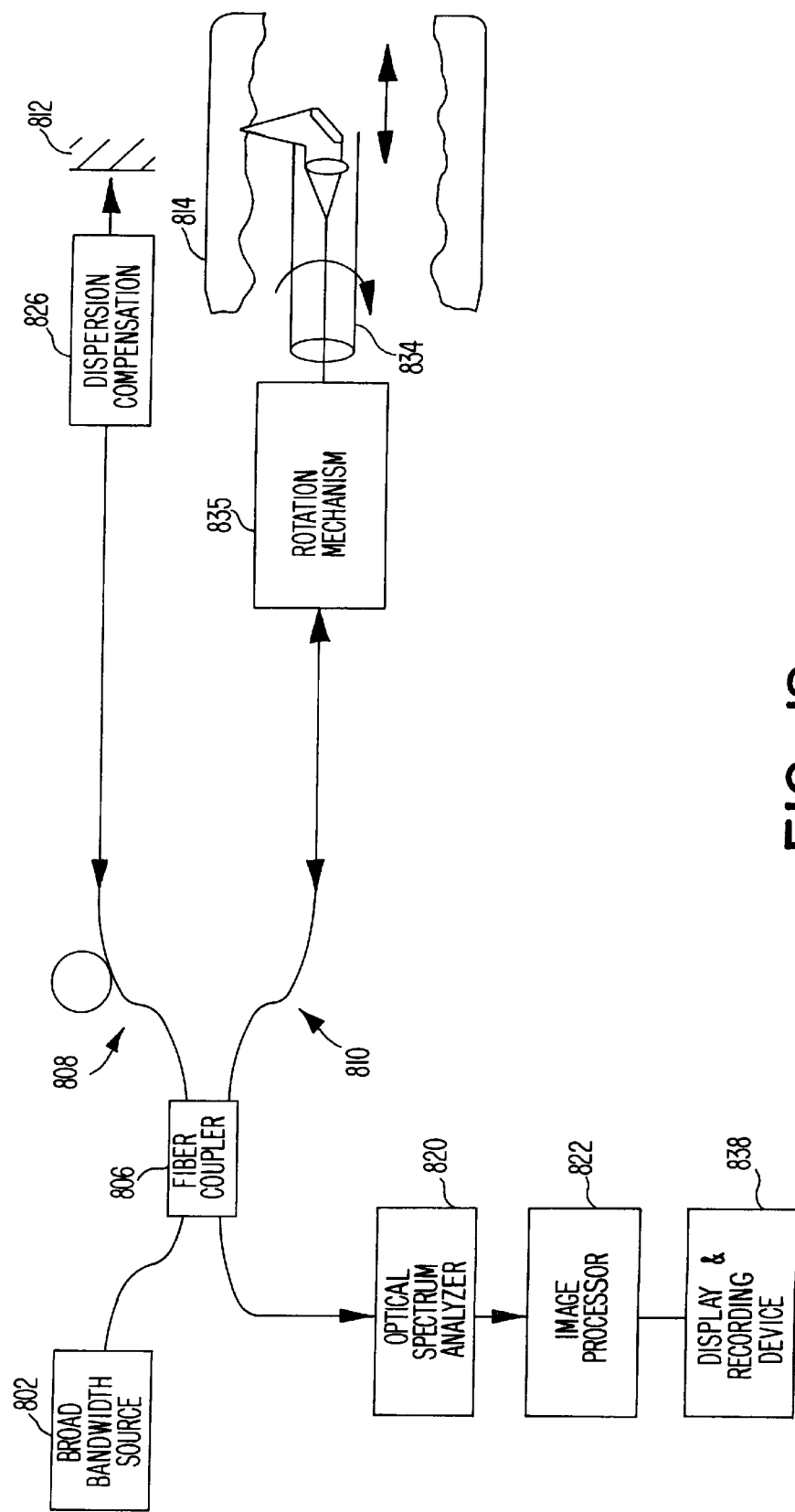
FIG. 18 depicts a non-longitudinal scanning embodiment of the imaging system of the present invention, utilizing a Fourier transform spectroscopy.

Although most of the above discussion has focused on methods that involve changing the length of the reference path through a longitudinal scanning mechanism, there are several embodiments of the present invention which do not employ a longitudinal scanning mechanism, particularly as described in FIG. 17 and FIG. 18. Referring to the embodiment of FIG. 17, the optical radiation source 702 is a narrow bandwidth frequency tunable source, such as a semiconductor laser with tunable external gratings, a tunable solid state laser (e.g. TiAlO3), or a dye laser. As the optical source 702 is tuned rapidly over a wide frequency range, longitudinal information about the structure 714 in question can be determined without the use of a longitudinal scanning mechanism. The radiation emitted by the sources 702 is transmitted to an optical coupler 706 which, as described previously, directs the radiation along an optical path defining the measuring arm 710 including a rotation mechanism 735 coupled to an endoscopic unit 734, and along an optical path defining the reference arm 708, including a dispersion compensation system 726, coupled to a static reference reflector 712, which is static during the measurement interval.

The constant power optical source 702 is rapidly frequency tuned over a wide frequency range in, for example, a sawtooth fashion, thus implementing a frequency chirp. In operation the measuring path 710 length is typically slightly longer than the reference path 708 length. Optionally, the reference reflector can be located at the end of the endoscope 734 as described in FIG. 2B. In such a case, the delay in time it takes light to travel from the source 702 to reference reflector 712 back to detector 716 with be slightly less than the delay from the source 702 to the sample 714 to detector 716, that is, a single reflection from within the structure 714 will arrive later than the reflection from the reference reflector 712. At detector 716 the two optical signals will interfere and the product of the two electric fields will be one component of interest generated in the detector 716. Because of the linear frequency chirp and the relative delay between the two optical fields, the product of the two fields will result in a constant beat frequency proportional to the relative distance of the reflection site within the structure 714 relative to the reference reflector 712. Defining Fm as the peak frequency deviation and T as the period of the frequency chirp, the beat frequency is given approximately by:

$$Fb \sim (Fm/T)*\Delta t \sim (Fm/T)*(2\Delta x/c),$$

where $\Delta t$ is the differential time delay between the two signals, $\Delta x$ is the differential effective optical path length, and c is the speed of light. Thus the beat frequency information contains the information concerning the optical path length of reflections within the structure 714. The magnitude of this beat-frequency term is proportional to the magnitude of the reflection site at that particular depth. Using a low noise transimpedance amplifier (TIA) 719 coupled to a RF spectrum analyzer 700 to perform RF spectrum analysis, a determination of the magnitude of the reflection over the frequency range of interest corresponding to the depth range of interest within structure 714 is made.

Referring to FIG. 18 another alternative embodiment of the invention is shown which eliminates the longitudinal scanning mechanism described above. In this embodiment the source 802 typically comprises a broad spectral bandwidth source. The need to adjust the path length of the reference arm 808, during the measurement interval is again eliminated and replaced with a static reference reflector 812. The radiation emitted by the sources 802 is transmitted to an optical coupler 806 which, as described previously, directs the radiation along an optical path defining the measuring arm 810 including a rotation mechanism 835 coupled to the endoscopic unit 834, and along an optical path defining the reference arm 808, including a dispersion compensation system 826, coupled to a static reference reflector 812. Optionally the reference reflector can be located at the end of the endoscope 834 as described in FIG. 2B.

In the embodiment shown, the detected radiation is analyzed in an optical spectrum analyzer 820 such as a grating based analyzer or a high finesse tunable fiber Fabry-Perot Filter. The output of the optical spectrum analyzer 820 becomes an input signal to a computerized image processor 822 which performs a Fourier transform of the spectrum at each rotational position to achieve an image of the structure in question. The output of the image processor 822 is directed to the display/recording device 838. In operation, the reflected radiation from the optical paths defining the reference arm 808 and measurement arm 810 are combined in the optical coupler 806 as discussed previously and transmitted to the spectrum analyzer 820. In one embodiment, the reference arm 808 path length is slightly less than the path lengths of interest to structure 814.

For purposes of discussion, assume there is a single reflection from within structure 814. Let the measuring arm 810 path length be the optical path length from the source 802 to structure 814 back to the input of the optical spectrum analyzer 820. Let the reference path 808 length be from optical source 802 to reference reflector 812 back to the input of the optical spectrum analyzer 820. The differential optical path length is the difference between the measuring and reference arm 810, 808 paths. The magnitude of the reflection in structure 814 and its associated differential path length can be measured by examining the optical spectrum. For a given differential optical path length there will be constructive and destructive optical interference across the frequencies contained in source 802, at optical spectrum analyzer 820. The magnitude of this interference will be dependent on the magnitude of the reflection. If there is no reflection, then there will be no interference. If the reflection is as large as the reference reflection, then there could be complete cancellation of the optical spectrum at particular frequencies.

In the absence of differential dispersion, which is compensated using dispersion compensator 826, the optical spectrum measured at the optical spectrum analyzer 820 will contain a sinusoidal interference pattern representing intensity versus optical source frequency. The magnitude of the interference pattern is proportional to the structure's reflection coefficient the frequency of which is proportional to the differential optical path length. The period of the interference pattern versus optical frequency is given by $\Delta f \sim \Delta x/c$, where $\Delta x$ is the differential optical path length. If there are many optical reflections (different $\Delta x$'s) at different depths within the structure 814, then there will be many sinusoidal frequency components. By performing a Fourier transform in the image processor 822, of the data derived in the optical spectrum analyzer 820 will provide a reflectivity profile of the structure 814.

System Use with Medical Procedures

The above-described embodiments of the present invention can be used with many types of minimally invasive medical procedures. The present invention can provide a method of intravascular high resolution imaging for intravascular stent deployment. The imaging system of the present invention can be integrated into a conventional stent catheter. High resolution imaging can be used to assess the position of the stent relative to the vessel or tissue wall, identify the presence of clot within the vessel or tissue wall, and to determine the effect of compression on vascular microstructure. Stent placement is currently followed with angiograms (as described above) and intravascular ultrasound. The limitations of intravascular ultrasound are the low resolution, lack of ability to distinguish clot from plaque, and inability to accurately assess the microstructure below the vessel or tissue wall.

Referring to FIG. 11B, a stent can be partially deployed by balloon 80. If the stent is made transparent or partially transparent then the imaging technique can be used to help place the stent. To help in stent placement and inspection, two or more sheaths or other smooth surfaces can separate torque cable 45 and intimal surface of catheter body 47 so as to allow the imaging apparatus to move along the fiber axis relative to an outer catheter. The outer catheter can be secured using the proximal balloons or other means. The imaging catheter can be manually or in an automated fashion moved to inspect the surface of the stent or produce an image set.

Alternatively, the imaging system of the present invention can be integrated into a conventional pericutaneous atherectomy catheter. Therefore, the movement of the atherectomy blade through the plaque can be monitored in real-time reducing the likelihood of damage to vulnerable structures. Further, high resolution imaging is currently not available to guide conventional rotoblade catheter removal of plaque. The procedure, which "grinds" the surface of the vessel or tissue, is currently guided with angiography. The low resolution guidance with angiography, in addition to the inability to perform cross sectional imaging, makes maneuvering of the catheter within the vessel or tissue difficult and somewhat hazardous. The imaging system of the present invention can be integrated into a conventional rotoblade catheter. The high resolution imaging will allow assessment of the depth of tissue removal. Furthermore, since the generation of large fragments during rotoblation is believed to result in some of the complications associated with the procedure, high resolution imaging will allow the generation of these particles to be traced.

The use of intravascular lasers is hindered by the inability to control the position of the beam in three directions. Currently, the procedure is guided with angiography, assessing the vessel or tissue in an axial manner rather than in cross section. Therefore, the radial angle of the beam can not be assessed with a high degree of accuracy. Simultaneous use of the imaging system of the present invention to guide the procedure will allow two and three dimensional assessment of the position of the atherectomy beam.

Figure 19:
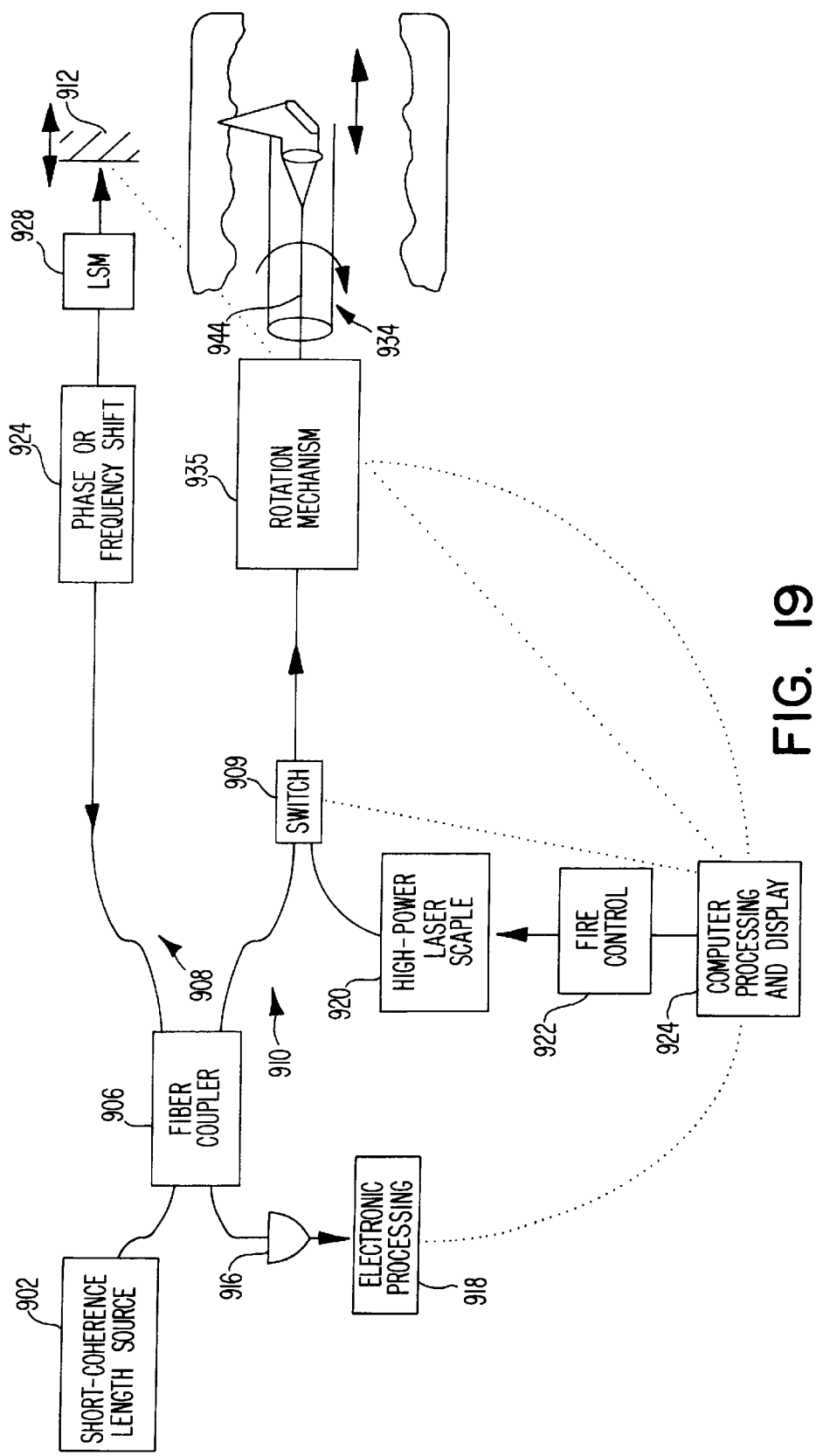
FIG. 19 depicts an alternate embodiment of the invention whereby the imaging system of the present invention is integrated with a laser surgical device.

Referring to FIG. 19, shown is an embodiment of the imaging system fiber-optically coupled laser surgical device 900. As described above, the imaging system includes a measuring arm 910 having a rotation mechanism 935 coupled to an endoscopic unit 934, and a reference arm 908 including a phase shifter 924, a longitudinal scanning mechanism 928 and a reference reflector 912. In this embodiment, a coupler or a high speed fiber-optic switch 909 can be used to couple the high power laser scalpel 920 with the endoscopic unit 934. If the laser scalpel 920 is of a different wavelength than it can be coupled using a WDM fiber optic coupler (not shown), to prevent optical interference at the detector 916 and allows simultaneous laser firing and imaging. In this embodiment, the firing of the laser scalpel 920 is controlled by firing control mechanism 922 which receives inputs from the computer 924. The computer 924 is coupled to the electronic processing unit 918 and provides such inputs in response to the imaging information obtained and displayed in processing unit 918 in near real-time. The laser scalpel 900 can deliver laser radiation from the laser source in laser scalpel 920 along the rotational setting selected by an operator using human information or using automated target recognition. The firing of the laser from laser source 902 is typically synchronized with the rotational scanning of the optical fiber 944 in the endoscopic unit 934, so that when a certain point on a structure 914 is being imaged, the laser is fired. Alternatively, the rotation could be stopped to allow continuous firing.

While the invention has been particularly shown and described above with reference to preferred embodiments, the foregoing and other changes in form and detail may be made therein by one skilled in the art without departing from the spirit and scope of the invention.

We claim:

1. An optical system for producing an image of an internal channel in situ, said optical system comprising:
   a short coherence length light source;
   a detector;
   an interferometer in optical communication with said light source and said detector, said interferometer comprising an adjustable optical delay device; and
   an endoscopic probe in optical communication with said interferometer,
   said detector detecting light altered by said internal channel in situ in response to said adjustable delay element to form an image of said internal channel in situ.

2. The optical scanning system of claim 1 wherein said endoscopic probe is an endoscope.

3. The optical scanning, system of claim 1 wherein said endoscopic probe is a catheter.

4. An optical system comprising;
   a short coherence length light source;
   a detector;
   an interferometer in optical communication with said light source and said detector, said interferometer comprising an adjustable optical delay device; and
   an optical probe in optical communication with said interferometer, said optical probe positioned to collect light altered by a sample in situ, said detector generating an image of said sample in response to said light altered by said sample in situ in response to changes in said adjustable optical delay device.

5. An optical system comprising:

a short coherence length light source producing broad band light;

a detector;

an interferometer in optical communication with said light source and in optical communication with said detector; and an optical probe in optical communication with said interferometer and positioned to receive broad band light altered by a sample in situ, said detector producing an image of said sample in situ in response to the spectral characteristics of said broad band light altered by said sample in situ.

6. The optical scanning system of claim 5 wherein said detector spatially disperses broad band light altered by said sample in situ and photodetects said spatially dispersed light.

7. An apparatus for performing imaging of a structure in situ comprising:

an optical radiation source;

a detector;

a processor in electrical communication with said detector;

an optical probe unit comprising:

an elongated housing defining a channel and having at least a portion which is at least partially transparent to light from said optical radiation source; and a beam director located within said housing and positioned to direct light to and from said structure in situ through said at least partially transparent portion;

an interferometer optically coupled to said radiation source, said optical probe unit, and said detector;

said detector generating a signal in response to radiation altered by said structure in situ; and said processor generating an image of said structure in situ in response to said signal from said detector.

8. The apparatus of claim 7, wherein said interferometer further comprises an adjustable optical delay in optical communication with said interferometer.

9. The apparatus of claim 7, wherein said detector comprises an optically dispersive element and an optical detector, and said processor produces images of said structure in situ in response to spectral signals from said detector.

10. The apparatus of claim 7, further comprising a Faraday Circulator positioned to direct radiation to said detector.

11. The apparatus of claim 7, wherein said optical probe unit further comprises a rotating optical system to scan said structure in situ through said at least partially transparent housing.

12. The apparatus of claim 7, wherein said elongated housing comprises a guidewire.

13. The apparatus of claim 7, wherein said optical probe unit further comprises an inflatable element affixed to said elongated housing.

14. The apparatus of claim 13 wherein said inflatable element is adjacent said at least partially transparent portion and said beam director directs light through said inflatable element.

15. The apparatus of claim 7 wherein said elongated housing is an endoscope.

16. The apparatus of claim 7 wherein said elongated housing is a catheter.

* * * * *

UNITED STATES PATENT AND TRADEMARK OFFICE
CERTIFICATE OF CORRECTION

PATENT NO. : 6,134,003
DATED : October 17, 2000
INVENTOR(S) : Tearney et al.

It is certified that error appears in the above-identified patent and that said Letters Patent is hereby corrected as shown below:

Title page, immediately below "Other Publications," insert:

--Mallery et al., "Assessment of normal and atherosclerotic arterial wall thickness with an intravascular ultrasound imaging catheter," Progress in Cardiology, *American Heart Journal*, Vol. 119, No. 6, pgs. 1392-1400 (1990).--

Under [63] Related U.S. Patent Application Data," replace entire paragraph and replace with:

--This application is a continuation-in-part of U.S.S.N. 08/916,759, filed on August 19, 1997, now U.S. Patent No. 5,784,352, which is a continuation of U.S.S.N. 08/492,738, filed on June 21, 1995, now abandoned; a continuation-in-part of U.S.S.N. 08/577,366, filed December 22, 1995, now U.S. Patent No. 5,748,598, and is a continuation-in-part of U.S.S.N. 08/252,940, filed June 2,1994, now abandoned, which is a continuation of U.S.S.N. 08/033,194, filed March 16, 1993, now U.S. Patent No. 5,459,570, which is a continuation of U.S.S.N. 07/092,877, filed April 29, 1991, now abandoned.--

Signed and Sealed this

Twenty-second Day of May, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 6,134,003
DATED : October 17, 2000
INVENTOR(S) : Tearney et al.

It is certified that error appears in the above-identified patent and that said Letters Patent is hereby corrected as shown below:

Column 1,
Line 23, after "Health," and before "and Contract Number", insert
-- grant F19826-95-C0002 by the United States Air Force, --.

Signed and Sealed this

Eleventh Day of December, 2001

*Attest:*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO.    : 6,134,003
DATED         : October 17, 2000
INVENTOR(S)   : Tearney et al.

It is certified that error appears in the above-identified patent and that said Letters Patent is hereby corrected as shown below:

Column 1,
Line 23, after "Health," and before "and Contract Number", insert
-- grant F19626-95-C-0002 by the United States Air Force, --.

This certificate supersedes Certificate of Correction issued December 11, 2001.

Signed and Sealed this

Thirtieth Day of April, 2002

*Attest:*

*Attesting Officer*

JAMES E. ROGAN
*Director of the United States Patent and Trademark Office*